US012419844B2

(12) United States Patent
De Smedt et al.

(10) Patent No.: US 12,419,844 B2
(45) Date of Patent: Sep. 23, 2025

(54) COMPOSITION FOR TREATMENT OF VITREOUS DISEASE OR DISORDER

(71) Applicants: UNIVERSITEIT GENT, Ghent (BE); UNIVERSITEIT ANTWERPEN, Antwerp (BE); UNIVERSITAIR ZIEKENHUIS ANTWERPEN, Edegem (BE)

(72) Inventors: Stefaan De Smedt, Mariakerke (BE); Felix Sauvage, Roubaix (FR); Kevin Braeckmans, Lokeren (BE); Katrien Remaut, Ghent (BE); Marie-José Tassignon, Berchen (BE); Juan Fraire, Brussels (BE); Jerry Sebag, Huntington Beach, CA (US)

(73) Assignees: UNIVERSITEIT GENT, Ghent (BE); UNIVERSITEIT ANTWERPEN, Antwerp (BE); UNIVERSITAIR ZIEKENHUIS ANTWERPEN, Edegem (BE)

( * ) Notice: Subject to any disclaimer, the term of this patent is extended or adjusted under 35 U.S.C. 154(b) by 742 days.

(21) Appl. No.: 17/283,103

(22) PCT Filed: Oct. 8, 2019

(86) PCT No.: PCT/EP2019/077248
§ 371 (c)(1),
(2) Date: Apr. 6, 2021

(87) PCT Pub. No.: WO2020/074532
PCT Pub. Date: Apr. 16, 2020

(65) Prior Publication Data
US 2021/0338595 A1    Nov. 4, 2021

(30) Foreign Application Priority Data
Oct. 8, 2018  (EP) .................................. 18199111

(51) Int. Cl.
*A61K 9/51* (2006.01)
*A61F 9/008* (2006.01)
*A61K 9/00* (2006.01)
*A61K 33/242* (2019.01)
*B82Y 5/00* (2011.01)

(52) U.S. Cl.
CPC ........ *A61K 9/5161* (2013.01); *A61F 9/00802* (2013.01); *A61F 9/00825* (2013.01); *A61K 9/0019* (2013.01); *A61K 9/0048* (2013.01); *A61K 33/242* (2019.01); *A61F 2009/00874* (2013.01); *B82Y 5/00* (2013.01)

(58) Field of Classification Search
CPC .. A61K 9/5161; A61K 33/242; A61K 9/0019; A61K 9/0048; A61F 9/00802; A61F 9/00825; A61F 2009/00874; B82Y 5/00
See application file for complete search history.

(56) References Cited

U.S. PATENT DOCUMENTS

| 2012/0191163 | A1* | 7/2012 | Yelin .................. | A61K 47/6923 977/773 |
| 2013/0120688 | A1* | 5/2013 | Chao ....................... | F21V 9/02 362/277 |
| 2015/0342678 | A1* | 12/2015 | Deladurantaye ........ | A61F 9/008 606/5 |
| 2017/0014401 | A1* | 1/2017 | Dalton ................ | C07D 217/24 |

FOREIGN PATENT DOCUMENTS

| WO | WO-2016109831 A1 * | 7/2016 | ........... A61B 5/0095 |
| WO | WO-2016163718 A1 * | 10/2016 | ............ A61K 47/30 |

OTHER PUBLICATIONS

Hyaluronic acid affinity for collagen; Hyaluronan Enhances Contraction of Collagen by Smooth Muscle Cells and Adventitial Fibroblasts Role of CD44 and Implications for Constrictive Remodeling Travis et al. Circulation Research. 2001;88:77-83 (Year: 2001).*
Machine translation for WO2016163718A1 (Year: 2016).*
International Search Report with Written Opinion from PCT Application No. PCT/EP2019/077248, Jan. 3, 2020.
Extended European Search Report from corresponding EP Application No. 18199111.8, Apr. 18, 2019.
Sebag, "Methodological and Efficacy Issues in a Randomized Clinical Trial Investigating Vitreous Floater Treatment," JAMA Ophthalmology, vol. 136, No. 4, Apr. 30, 2018, pp. 447-449.
Leonard et al., "Refractive Indices of the Collagen Fibrils and Extrafibrillar Material of the Corneal Stroma," Biophysical Journal, vol. 72, Mar. 31, 1997, pp. 1382-1387.
Xu et al., "Electromagnetic Scattering by an Aggregate of Spheres: Theoretical and Experimental Study of the Amplitude Scattering Matrix," Physical Review E, vol. 58, No. 3, Sep. 30, 1998, pp. 3931-3948.
Sebag et al., "Vitrectomy for Floaters—Prospective Efficacy Analyses and Retrospective Safety Profile," Retina, The Journal of Retinal and Vitreous Diseases, vol. 34, No. 6, at least as early as Dec. 31, 2014, pp. 1062-1068.
Chettiar et al., "Internal Homogenization: Effective Permittivity of a Coated Sphere," Optics Express, vol. 20, No. 21, Oct. 8, 2012, pp. 22976-22986.

* cited by examiner

*Primary Examiner* — Robert A Wax
*Assistant Examiner* — John W Lippert, III
(74) *Attorney, Agent, or Firm* — Workman Nydegger

(57) ABSTRACT

A composition includes particles for use in a method for the treatment of a vitreous disease or a vitreous disorder as a light sensitizing agent. Each particle has a surface selected for or adapted for providing mobility of the particle in the vitreous and for binding to collagen aggregates, such as floaters.

12 Claims, 14 Drawing Sheets

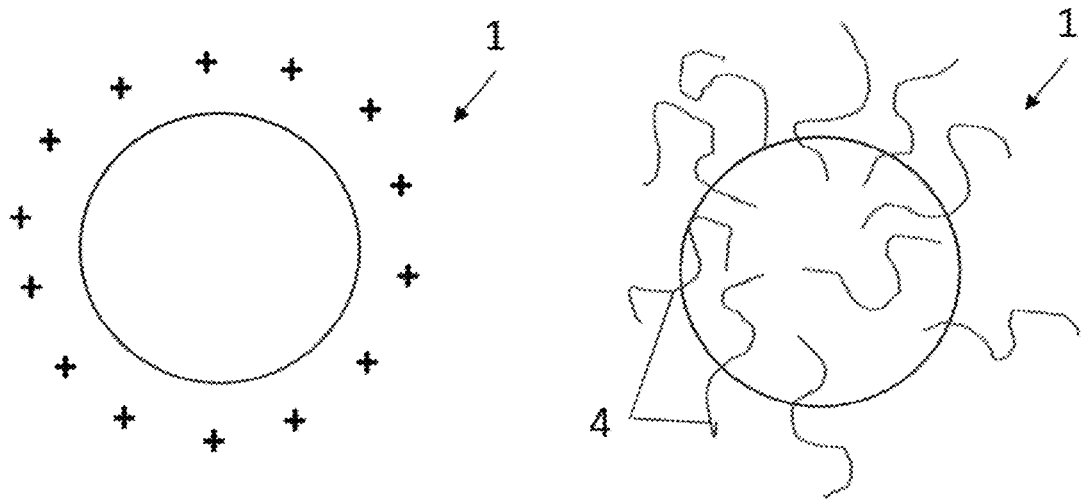
FIG 2  FIG 3
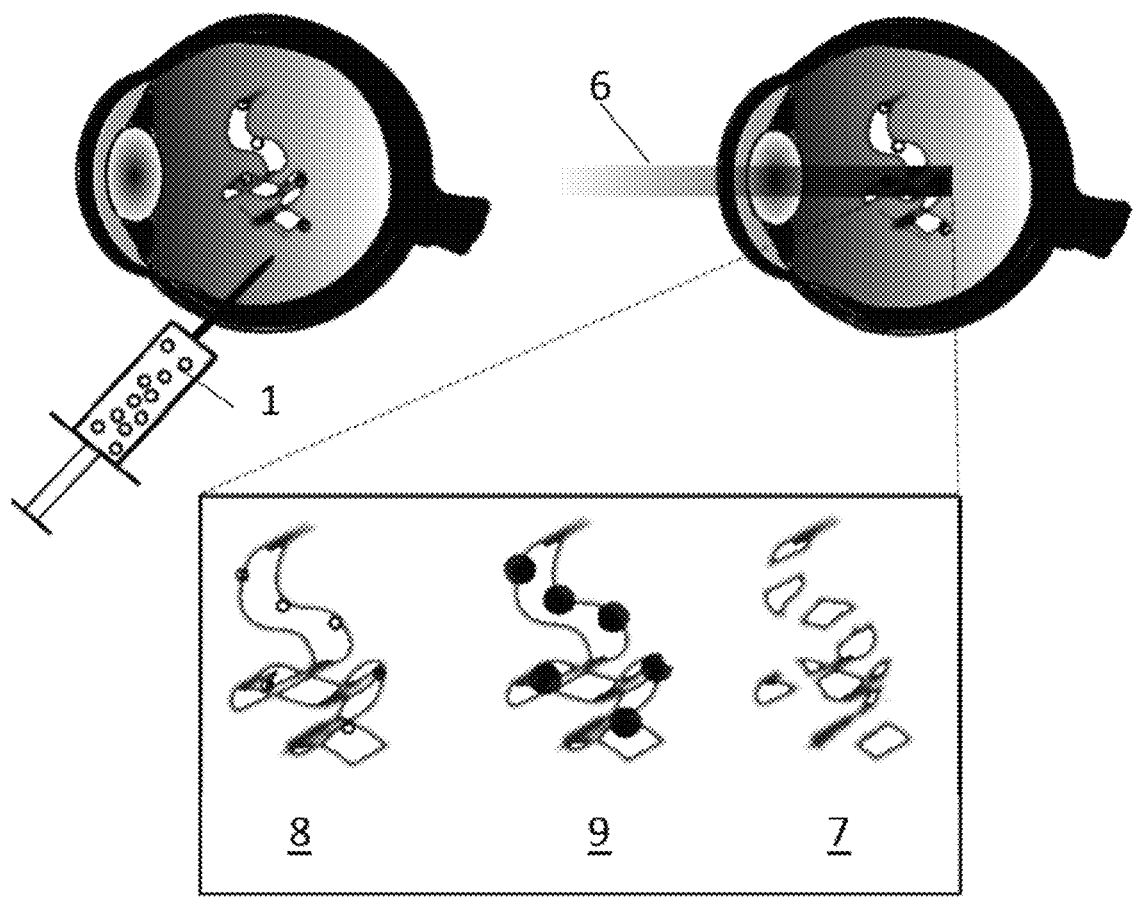
FIG 4

COMPOSITION FOR TREATMENT OF VITREOUS DISEASE OR DISORDER

FIELD OF THE INVENTION

The invention relates to the field of compositions for use in a medical treatment of vitreous diseases and/or disorders. More specifically it relates to a composition comprising particles for use in a method for the treatment of a vitreous disease or a vitreous disorder as a laser light sensitizing agent.

BACKGROUND OF THE INVENTION

Vitreous disorders can cause myodesopsia. When myodesposia is accompanied by degradation in contrast sensitivity function, it is called Vision Degrading Vitreopathy. The following describes vitreous composition and structure, changes with aging, myopia, and disease, and how these changes impact vision. A need exists in the art for new treatment modalities that could significantly improve upon current techniques.

Proteins are important in living organisms, as they are involved in structural functions and play a role in many physiological processes. In some situations, misfolded or unfolded proteins can accumulate and form toxic biological aggregates which are involved in many diseases. For example, protein aggregate may form in the vitreous body of the human eye.

The human vitreous body is a clear gel composed of water, different types of collagen, and hyaluronic acid (HA). In youth, collagen fibrils and HA form a supramolecular network that maintains transparency and confers a gel state to the vitreous body. The outer layer comprises densely-packed collagen fibrils, known as the posterior vitreous cortex, which is firmly adherent to the retina. The thus-formed collagen based structure is also called the collagen network.

With aging, re-organization of the molecular components in the vitreous body alters vitreous structure inducing gel liquefaction (synchysis senilis). This liquefaction is often accompanied by a collapse of the collagen network that could induce the formation of other collagen-based structures in the form of light scattering opacities responsible for the phenomenon of floaters or by a posterior vitreous detachment (PVD). More in detail, dissociation of HA from collagen allows the fibrils to cross-link and aggregate into bundles of collagen fibrils. There is also concurrent weakening of vitreo-retinal adhesion, which in conjunction with gel liquefaction results in posterior vitreous detachment, the most common cause of myodesopsia.

Typically, intravitreal collagen aggregates cause light scattering and other optical aberrations in the eye that induce the clinical phenomenon of myodesopsia, commonly referred to as floaters, eye floaters, or vitreous floaters. The fibrillar structures that cause floaters are aggregates of vitreous collagen, either within the vitreous body, most often associated with myopia, or arising from the dense collagen matrix of the posterior vitreous cortex that separates from the retina in age-related PVD. These collagenous aggregates scatter light and cast shadows on the retina, which are perceived by the patient as grey objects of different sizes and shapes.

Although myodesopsia was previously not considered a serious problem in ophthalmology, many patients with symptomatic vitreous floaters experience a significantly negative impact on their quality of life. In terms of vision, studies have shown that while there can be slight loss of visual acuity, there is significant degradation in contrast sensitivity function, which likely accounts for profound unhappiness in some cases. Therefore, this represents an unmet medical need.

Unfortunately, methods of treating this disorder are presently limited to either Nd:YAG laser treatment, which has never been definitively shown to be effective, and vitrectomy which is invasive and costly. While pharmacologic vitreolysis has demonstrated efficacy in other applications, this is not the case for myodesopsia. Thus, patients are often advised to cope with their symptoms without any treatment. For some patients, reassurance and a psychological approach may be helpful. For many, however, the effects of such symptoms can be quite severe, e.g. curtail outdoor activities, the necessity to wear sunglasses outdoors and even indoors under fluorescent lighting and in rooms with windows. Myodesopsia may prevent a patient to drive a vehicle, or may severely complicate driving a vehicle, e.g. by requiring a constantly heightened level of concentration. Driving at night may be difficult or even impossible due to glare effects of headlights reflections. Other difficulties may include problems with reading. Modern life involves extensive use of computers, whose back-lit screens exaggerate the effects of vitreous floaters. In some cases, patients can temporarily alleviate the effects of floaters by a transfer of momentum to the floaters, e.g. by frequently applying sudden movements of the eyes or the head. But this can be a very frustrating way to live. Recent studies employing objective quantitative measure of vitreous structure with ultrasonography and visual function with contrast sensitivity testing have enabled the identification of clinically significant cases.

When the treatment of Vision Degrading Myodesopsia is considered feasible and advisable, e.g. for highly symptomatic patients, it is known in the art to perform a vitrectomy, i.e. a pars plana vitrectomy (PPV) in which the vitreous is removed and replaced with a buffered saline solution, see e.g. Sebag et al, "Vitrectomy for floaters: prospective efficacy analyses and retrospective safety profile," in Retina 34:1062-68, 2014. However, such procedures are invasive and may cause other effects that reduce the quality of vision, such as cataracts. Furthermore, although a high rate of patient satisfaction can be achieved, vitrectomy can be associated with complications such as retinal tears/detachments or endophthalmitis.

Another treatment known in the art is ablation of the floater-causing opacities in the vitreous body by a laser treatment, i.e. laser vitreolysis. For example, an yttrium aluminium garnet (YAG) laser, e.g. an Nd:YAG laser, may be used for such laser treatment. In such an approach, vitreous opacities are targeted by a large number of laser pulses to locally raise the temperature (e.g. up to a few thousand K), which results in plasma production and optical breakdown of the vitreous opacities. Although being less invasive than vitrectomy, laser vitreolysis is difficult to employ for the clinician, since it may be difficult to specifically target the floater-causing vitreous opacities, e.g. the floater-causing opacities may be difficult to access for the laser treatment. Furthermore, such therapy has never been conclusively shown to be effective, see e.g. Sebag et al, "Methodological and efficacy issues in a randomized clinical trial investigating vitreous floater treatment," JAMA Ophthalmol 136(4):448, 2018. A retrospective study found that 38% of patients treated with a YAG laser treatment had moderate improvement in symptoms as compared to full resolution of symptoms in 93% of eyes treated with PPV. A recent randomized clinical trial comparing YAG vitreolysis of only Weiss Rings (and not all vitreous opacities) with sham YAG vitreolysis in 52 patients reported that only 54% of patients had improvement in their symptoms and by only 53% as compared to controls. The shape, size, and location of the vitreous opacities causing floaters can have an impact on the efficacy of laser treatment, thereby necessitating a trial and error approach based on the practitioner's observation and judgement. Therefore, a need exists for more effective and efficient laser treatment of vitreous opacities that cause Vision Degrading Myodesopsia.

SUMMARY OF THE INVENTION

It is an object of embodiments of the present invention to provide a solution for treatment of vitreous diseases and/or disorders, such that such treatment can be performed in an efficient and/or effective manner and/or with only a limited risk for further complications, side effects and/or damage to eye.

The above objective is accomplished by a method and device according to the present invention.

It is an advantage of embodiments of the present invention that a good treatment of vitreous opacities can be achieved, regardless of the shape, the size and the location of the floater-causing opacities in the vitreous body.

It is an advantage of embodiments of the present invention that good access of the laser to the vitreous in a laser treatment can be achieved.

It is an advantage of embodiments of the present invention that treating vitreous opacities by using a pulsed nanosecond, picosecond or femtosecond laser can offer better access of the laser to the vitreous, e.g. as compared to a YAG laser treatment as known in the art. It is also an advantage that the use of pulsed femtosecond lasers has already been approved for use in ophthalmology, e.g. is commonly used for cataract and corneal surgery.

It is an advantage of embodiments of the present invention that a laser treatment can be improved, compared to techniques known in the art, by using a conventional laser approved for use in ophthalmology.

It is an advantage of embodiments of the present invention that a safer therapy can be achieved by decreasing, even strongly decreasing, laser intensity, relative to prior art approaches.

It is an advantage of embodiments of the present invention that specific targeting of collagen in floater-causing vitreous structures can be achieved, thus reducing damage to the retina, lens, and/or the vitreous body.

It is an advantage of embodiments of the present invention that complications for the patient can be reduced.

In a first aspect, the present invention relates to a composition comprising particles for use in a method for the treatment of a vitreous disease or a vitreous disorder as a light sensitizing agent. Each particle comprises a surface selected for or adapted for providing mobility of the particle in the vitreous body and for binding to collagen aggregates. It is unexpected that, despite the increased mobility, a good binding to the collagen aggregates occurs.

The particles may be selected to be made out of material which is mobile in vitreous and binds to collagen aggregates. In this case, the particles have a surface that is "selected for" providing mobility and for binding to collagen aggregates. Alternatively, the particles may comprise a core of any suitable material, and be coated on their outer surface with a material that has the above properties, in which case the surface is "adapted for" providing mobility and for binding to collagen aggregates.

In a composition in accordance with embodiments of the present invention, the coating may be a negatively charged coating.

In a composition in accordance with embodiments of the present invention, the coating may be an anionic hydrophilic coating. It is an advantage of an anionic hydrophilic coating that good mobility through vitreous can be achieved, and that aggregation of the particles at an injection site may be prevented or reduced.

For example, in a composition in accordance with embodiments of the present invention, the coating may comprise poly(ethylene)glycol (PEG) and/or a derivative thereof.

For example, in a composition in accordance with embodiments of the present invention, the coating may comprise hyaluronic acid and/or a derivative thereof. It is an advantage of a hyaluronic acid (or derivative) coating, that hyaluronic acid is a natural component of the vitreous, and therefore reduces the risk of undesirable and/or unpredictable interactions with the vitreous medium.

In a composition in accordance with embodiments of the present invention, the particles may be adapted for forming vapor nanobubbles in the vitreous when introduced therein and being irradiated with radiation such as laser light. Hereto, the particles have the capacity to efficiently absorb the energy of radiation, e.g. light, within a certain wavelength range and transform that energy into heat or the formation of a plasma, which in turn can cause the liquid (e.g. water in hydrated biological tissue) surrounding the particles to evaporate, resulting in the formation of vapour nanobubbles.

The particles, for instance their core, may comprise or consist of a material suitable for the formation of light-induced mechanical forces.

The core may have any suitable shape, for instance but not limited thereto, the core may be a spherical object, a rod-shaped object, a star-shaped object, a pyramid-shaped object. The core may consist of multiple parts; for instance a silica core may be combined with a material suitable for vapour nanobubble formation. In a composition in accordance with embodiments of the present invention, the particles, in particular for instance their core, may comprise or consist of a plasmonic metal, such as gold, platinum or silver.

In a composition in accordance with embodiments of the present invention, the particles, in particular for instance their core, may comprise a polymer material, carbon and/or titanium. The core may comprise melanin. The core may comprise poly-DOPA.

In a composition in accordance with embodiments of the present invention, the particle (or the core) may be a nanoparticle or microparticle.

In a composition in accordance with embodiments of the present invention, the particle (or the core) may be a nanosphere or microsphere. The particle (or the core) may also be a nanorod, a microrod, a nanostar, a microstar, a nanopyramid, a micropyramid, a nanoshell or a microshell.

In a composition in accordance with embodiments of the present invention, the particles may have a diameter in the range of 1 nm to 1000 nm, such as 1 nm to 500 nm, for instance in the rage of 1 nm to 100 nm, e.g. in the range of 1 nm to 50 nm. In embodiments of the present invention, the particles may have a diameter in the range of 2 nm to 500 nm, preferably in the range of 5 nm to 100 nm, e.g. in the range of 10 to 80 nm. It is particularly useful to use small particles, which typically have a higher mobility in the vitreous. Smaller particles have a smaller effect in terms of generation of vapour bubbles and the strength thereof to locally exert a mechanical force in the vitreous; however, more of these smaller particles can bind to collagen aggregates, such that their combined effect of exerting a mechanical force can be at least as big, if not bigger, as when using larger particles.

In a second aspect, a composition in accordance with embodiments of the present invention, may be used in a method for treatment of a vitreous disease or vitreous disorder, such as for instance myodesopsia. e.g. the perception of floaters and, if severe, Vision Degrading Vitreopathy. For example, in myodesopsia, collagen aggregates may form linear, membranous, or netlike masses that are very disruptive to normal vision. A floater may be defined as a spot that appears to drift in front of the eye, caused by a shadow cast on the retina by vitreous opacities. Floaters may be caused by embryological remnants or can be acquired due to aging, trauma, iatrogenic, ocular or systemic metabolic pathologies. The perception of a floater may be characterized by shadow-like vision artefacts. Furthermore, floaters are most commonly a result of aging and posterior vitreous detachment, often occurring in middle age. In younger subjects, floaters are most commonly caused by myopic vitreopathy.

A composition according to embodiments of the first aspect of the present invention may be used as a light sensitizing agent in a method for the treatment of a vitreous disease or a vitreous disorder.

The treatment may be, or may comprise, a laser ablation treatment, after injection of the composition into the vitreous body of an eye of a human or animal subject. The treatment may comprise injecting the composition into the vitreous body of an eye of a human or animal subject.

When using the composition in accordance with embodiments of the first aspect of the present invention, the particles may specifically bind to collagen or collagen based structures in the vitreous body and may locally exert a mechanical force in the vitreous when irradiated by laser light in the laser ablation treatment.

When using the composition in accordance with embodiments of the first aspect of the present invention, the particles may form vapor nanobubbles in the vitreous when being irradiated, so as to exert a mechanical force onto the collagen.

When using the composition in accordance with embodiments of the first aspect of the present invention as a light sensitizing agent in a method for treatment of a vitreous disease or a vitreous disorder, the particles may cluster around a vitreous opacity to concentrate energy deposition by the laser ablation treatment near and/or in the vitreous opacity, such that a collapse of the vapor nanobubbles releases a mechanical force to dislodge and/or break apart the vitreous opacities. The smaller the size of the particles used, the more particles may cluster around the vitreous opacity.

The laser ablation treatment may comprise irradiating at least part of the vitreous body by laser pulses.

The laser pulses may consist of one to 100 laser pulses, e.g. one to 20 laser pulses, per vitreous opacity.

The laser pulses may have a duration in the range of 10 fs to 1000 ns, for instance in the range of 10 fs to 10 ns, e.g. in the range of 10 fs to 1 ps or in the range of 1 ps to 10 ns.

The laser pulses may each have a power density in the range of $10^7$ to $10^{15}$ W/cm$^2$, e.g. in the range of $10^{12}$ to $10^{15}$ W/cm$^2$, or alternatively expressed a fluence in the range of 10 µJ/cm$^2$ to 100 J/cm$^2$, e.g. in the range 10 mJ/cm$^2$ to 10 J/cm$^2$.

The vitreous opacities being treated may have a length in the range of 1 mm to 3 mm, embodiments of the present invention not necessarily being limited thereto.

The vitreous opacities being treated may be close to the retina or to the lens, e.g. at a distance in the range of 0 mm to 5 mm. For example, the floater may be present in the bursa premacularis. However, embodiments of the present invention are not necessarily limited to treating vitreous opacities that are close to the retina or eye lens.

In a third aspect, the present invention provides a method of ablation of vitreous opacities, the method comprising the steps of injecting into the vitreous a composition according to embodiments of the first aspect, specifically binding the particles of the composition to collagen aggregates in the vitreous, and locally exerting a mechanical force in the vitreous by irradiating the particles with laser light.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 2 schematically illustrates a particle in a composition for use in the treatment of a vitreous disease and/or disorder in accordance with embodiments of the present invention, the particle comprising a cationic coating.

FIG. 3 schematically illustrates a particle in a composition for use in the treatment of a vitreous disease and/or disorder in accordance with embodiments of the present invention, the particle comprising a hyaluronic acid coating.

FIG. 4 schematically illustrates a use of a composition in the treatment of a vitreous disease and/or disorder in accordance with embodiments of the present invention, the treatment comprising injecting the composition into the vitreous and irradiating the vitreous or part thereof by a laser.

Figure 1:
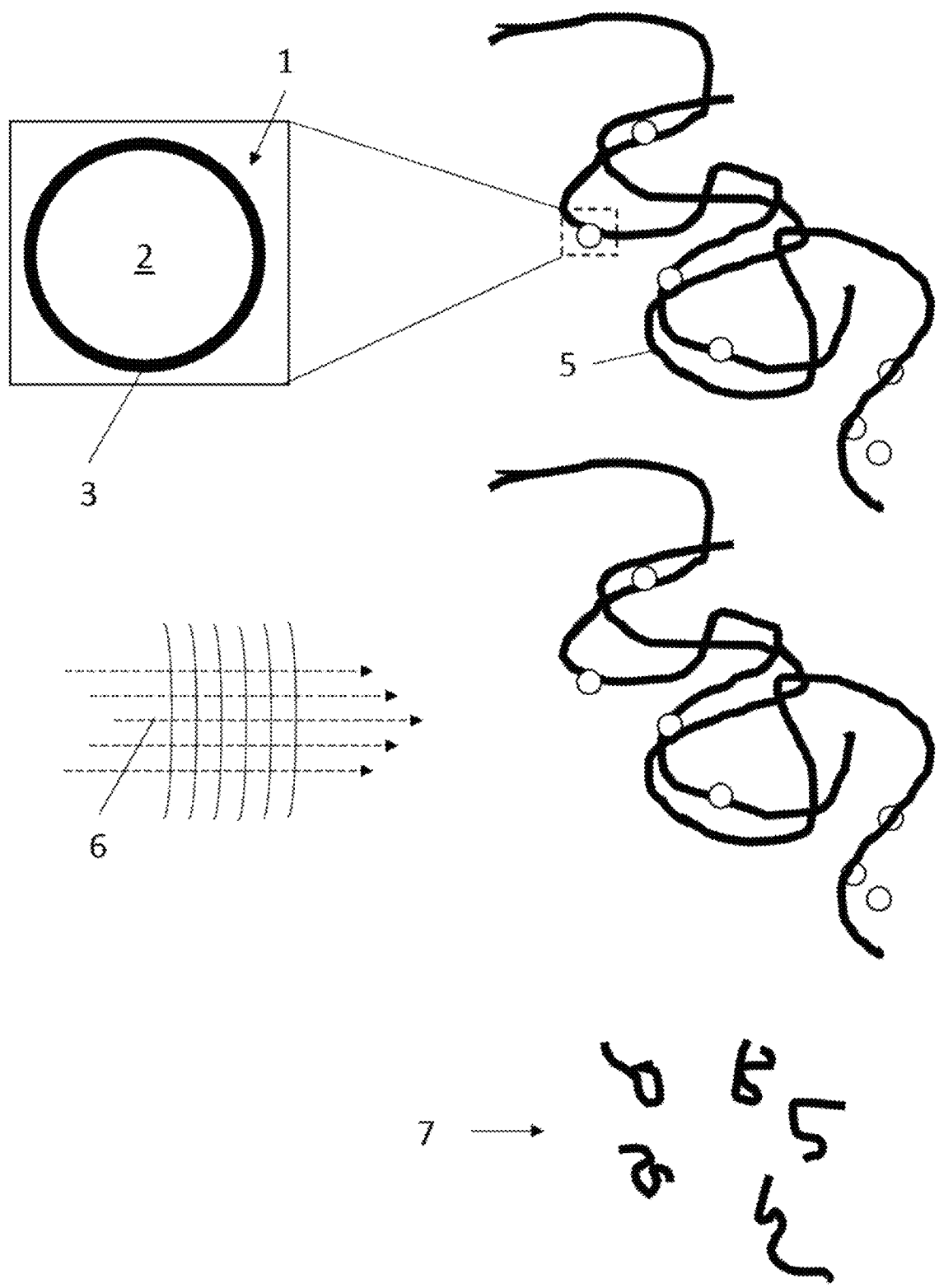
FIG. 1 schematically illustrates a particle in a composition for use in the treatment of a vitreous disease and/or disorder in accordance with embodiments of the present invention, and the use thereof.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. The term "comprising" therefore covers the situation where only the stated features are present and the situation where these features and one or more other features are present. Thus, the scope of the expression "a device comprising means A and B" should not be interpreted as being limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. For instance, in what follows, reference is made to particles having a coating with particular characteristics of mobility and binding. However, as explained above and as reflected in the claims, the present invention is not limited thereto, and covers also particles which inherently have these characteristics at their surface, e.g. because they have these characteristics throughout their core.

In other instances, well-known methods, structures and techniques have not been shown in detail in order not to obscure an understanding of this description.

Where in embodiments of the present invention reference is made to "myodesopsia", reference is made to the perception of floaters. The perception of a floater may be characterized by shadow-like vision artefacts.

Where in embodiments of the present invention reference is made to a "floater" or "vitreous floater," reference is made to a vitreous disorder in which the vitreous network is disrupted, e.g. by aggregates of collagen adhering to the vitreous framework in netlike masses that are disruptive of normal vision. A floater may be perceived as a linear structure with nodules, or a meshwork of linear structures, that appears to drift in front of the eye, caused by a shadow cast on the retina by vitreous opacities. Floater-causing vitreous opacities may be caused by embryological remnants, or may be acquired due to aging, trauma, iatrogenic, ocular or systemic metabolic pathologies.

The present invention relates to a composition comprising particles for use in a method for the treatment of a vitreous disease or a vitreous disorder as a light sensitizing agent, e.g. a laser-light sensitizing agent. Each particle comprises a coating adapted for providing mobility of the particle in the vitreous and for binding to collagen aggregates, e.g. collagen fibers.

An advantageous approach for the treatment and destruction or ablation of vitreous opacities and/or floaters, such as macroscopic floaters (e.g. having a length in the range of 0.5 mm to 5 mm, e.g. around 1 mm) is demonstrated in the present specification.

Laser irradiation, such as laser irradiation by pulsed lasers, e.g. pico-, femto- and/or nanosecond pulsed lasers, can be combined with a laser sensitizing agent in accordance with embodiments of the present invention to efficiently destroy collagen fibers in the vitreous, e.g. by laser-induced vapor nanobubble generation. Furthermore, as detailed hereinbelow, hydrophilic anionic coating of the nanoparticles, e.g. of gold nanoparticles, may provide an advantageously high diffusion in the vitreous, such that accumulation after injection (e.g. at the injection site) can be avoided or reduced and/or such that a good binding of the nanoparticles to targeted structures, e.g. floaters, can be achieved. However, while laser irradiation may be advantageous, irradiation by another (intense) light source is not necessarily excluded to achieve the same or similar effects.

Compared to prior-art laser treatments of vitreous opacities and/or floaters, e.g. using an Nd:YAG laser therapy, a greater efficacy may be achieved. Furthermore, fewer laser pulses and/or a lower laser energy can be used to destroy floater-causing vitreous opacities when compared to the conventional laser therapy (e.g. which may typically require up to 8 mJ and 200 pulses). Furthermore, the laser irradiation in a use in accordance with embodiments of the present invention may be performed using a laser emitting laser light in the visible spectrum, e.g. a wavelength of 561 nm, which advantageously makes the light visible to the clinician, e.g. as opposed to a prior-art Nd:YAG laser treatment to treat eye floaters that operates at 1064 nm, outside the visible spectrum. This may advantageously avoid the use of additional visualization means, such as a coaxial red helium neon laser beam for indicating the targeted position.

Referring to FIG. 1, a particle 1 in a composition for use in a method for the treatment of a vitreous disease and/or disorder in accordance with embodiments of the present invention is shown.

Each particle 1 may comprise a core 2. In embodiments of the present invention, the invention not being limited thereto, each particle comprises a coating 3, e.g. provided on an exterior surface of the core. The coating is adapted for providing mobility of the particle 1 in the vitreous and for binding to collagen aggregates 5. This good binding to collagen aggregates despite the increased mobility of the particles through the vitreous, is unexpected and brings the advantageous effects of the present invention.

The core 2 may advantageously absorb laser irradiation, e.g. such as to locally enhance the energy deposition by laser. For example, the core may provide a surface plasmon resonance effect to advantageously locally enhance laser energy absorption. For example, the core may comprise a noble metal, such as gold, which has such advantageous surface plasmon resonance properties. The particles may bind to collagen fibres, e.g. vitreous floaters, and may be heated up to break or dislodge collagen aggregates, e.g. by locally generating vapor nanobubbles (VNBs).

It is an advantage that the particles may diffuse through the vitreous efficiently, and locally bind to collagen. Particularly, the particles may bind to collagen of floater structures to be destroyed by a laser irradiation 6. It is an advantage of the particles that these may generate a localized mechanical force in the vitreous when exposed to the laser light irradiation 6, e.g. while bound to a collagen structure. For example, upon laser illumination (e.g. pulsed laser, such as nanosecond laser pulses), the particles bound to the collagen quickly heat up to several hundred degrees. Consequently, the water of the surrounding environment evaporates to form VNBs emerging around the surface of the particles. Such VNBs will first expand and then collapse thereby generating high-pressure shockwaves, providing a localized mechanical force.

Thus, the released mechanical force can break collagen fibers apart 7, such that the collagen fragments influence the optical transmission of light through the eye in a lesser extent. Furthermore, the smaller collagen fragments may disperse through the eye to reduce local vision artefacts and/or may sediment such as not to substantially affect the vision.

In a composition for the use in accordance with embodiments of the present invention, the coating may be adapted for providing a good mobility of the particle in the vitreous. The coating may be an electrostatic coating.

For example, the coating may comprise a cationic coating, e.g. as illustrated in FIG. 2, e.g. a poly(diallyldimethylammonium chloride) (PDDAC) coating.

The coating may be an anionic hydrophilic coating. It is an advantage of such anionic hydrophilic coating that a good mobility in the vitreous can be achieved.

In a composition for the use in accordance with embodiments of the present invention, the coating may comprise poly(ethylene)glycol (PEG) and/or a derivative thereof.

Furthermore, the core material, such as gold, may advantageously bind well to collagen fibers. This effect can be observed for different size ranges of the particle and different surface charge states.

Referring to FIG. 3, in a composition for the use in accordance with embodiments of the present invention, the coating may comprise hyaluronic acid 4 (hyaluronan, sodium hyaluronate) and/or a derivative thereof.

In a composition for the use in accordance with embodiments of the present invention, the core may comprise or consist of a noble metal, such as gold, platinum or silver. Alternatively, the core may comprise a polymer material, carbon, iron oxide, titanium oxide, e.g. $TiO_2$, and/or titanium.

In a composition for the use in accordance with embodiments of the present invention, the particle may be a nanoparticle or microparticle.

In a composition for the use in accordance with embodiments of the present invention, the particle may be a nanosphere.

In a composition for the use in accordance with embodiments of the present invention, the particle may have a diameter in the range of 1 nm to 1000 nm, for instance 1 nm to 500 nm, e.g. in the range of 1 nm to 100 nm, preferably in the range of 1 nm to 50 nm, e.g. in the range of 1 nm to 20 nm. In embodiments of the present invention, the particle may have a diameter in the range of 2 nm to 500 nm, for instance 5 nm to 100 nm, such as 10 nm to 80 nm.

It is an advantage of smaller particle sizes, e.g. in the range of 1 nm to 50 nm, e.g. in the range of 1 nm to 20 nm that the mobility of the particles in the vitreous may be improved. Furthermore, a plurality of the particles may bind to a collagen structure of a floater, such as to locally cluster around the floater. Thus, the local energy deposition by laser excitation can be enhanced near or at the floater, while releasing energy to a lesser, or no substantial, extent throughout the vitreous where the particles do not cluster.

For example, the cores may be manufactured using the Turkevich method, as known in the art. The Turkevich method is based on the reduction properties of boiling citrate solutions. For example, gold nanoparticles may be synthesized, e.g. having a diameter in the range of 70 nm to 80 nm. In this example, a 150 mL 0.2 mM chloroauric acid solution ($HAuCl_4$) may be reduced by the addition of 0.5 mL of a 0.01 M citrate solution (corresponding to a 1:1 Au/Citrate molar ratio) under heat and rapid stirring for 30 min. Particles may be overgrown to the desired size by addition of $Au^{3+}$ and ascorbate solutions through capillary tubes and controlling the maximum in the Extinction spectrum by UV-vis spectroscopy. When the dipolar LSPR peak matched the LSPR peak of a predetermined desired size (e.g. between 538 nm and 542 nm for a particle size in the range of 70 nm to 80 nm) the synthesis can be stopped.

As another example, 10 nm gold nanoparticles may be synthesized using ascorbate as reducing agent. A typical synthesis may consist of adding Au to give a final concentration of 0.2 mM chloroauric acid solution ($HAuCl_4$) with the addition of equimolar quantities of sodium ascorbate (final volume=100 mL) under rapid stirring and a reaction time of 30 min.

The particles, e.g. the particle size, may be characterized by UV-vis spectroscopy, dynamic light scattering (DLS), transmission electron microscopy (TEM), and/or electrodynamic modeling using Mie theory. The obtained concentration of the particles may be estimated using experimental extinction intensities at the maximum wavelength, and Mie theory calculations of the extinction cross section for spherical particles.

The coating may be provided on the particle core in accordance with known processes. For example, the particle cores may be functionalized with HA or PDDAC to achieve respectively negative or positive zeta potentials. Functionalization with HA may be performed by adding 3 mg of the polymer per 50 mL of a stock solution of the particles (e.g. a stock solution of the synthetized particles in pM concentration). Likewise, functionalization with PDDAC may be performed by addition of the polymer to a final concentration of 11.9 mg/mL to 50 mL of the synthetized particles. After reaction, e.g. overnight, the functionalized particles may be washed by centrifugation (e.g. 10 min at 13000 g for 10 nm particles and 5 min at 2000 g for 70-80 nm particles) and resuspended in water. Successful functionalization can be confirmed by DLS size and zeta potential measurements.

In a composition for the use in accordance with embodiments of the present invention, the vitreous disease or vitreous disorder may be myodesopsia.

In a composition for the use in accordance with embodiments of the present invention, the treatment may be, or may comprise, a laser ablation treatment 6. The treatment may comprise injecting the composition 1 into the vitreous of an eye of a human or animal subject, as illustrated in FIG. 4.

A composition for use in accordance with embodiments of the present invention may have a concentration in the range of $10^9$ to $10^{14}$, e.g. in the range of $10^{10}$ to $10^{12}$, particles per ml.

In a composition for the use in accordance with embodiments of the present invention, the particles may be used for specifically binding to collagen in the vitreous, for example in the collagen fibers 8 causing vitreous opacities, and for locally exerting a mechanical force in the vitreous when irradiated by laser light in the laser ablation treatment.

In a composition for the use in accordance with embodiments of the present invention, the particles may be adapted for forming vapor nanobubbles 9 in the vitreous to exert the mechanical force. Thus, the released mechanical force can break collagen fibers apart 7.

In a composition for the use in accordance with embodiments of the present invention, the particles may be adapted for clustering around a vitreous floater to concentrate an energy deposition by the laser ablation treatment near and/or in the vitreous floater, such that a collapse of the vapor nanobubbles releases a mechanical force to dislodge and/or break apart the vitreous floater.

In a composition for the use in accordance with embodiments of the present invention, the laser ablation treatment may comprise irradiating at least part of the vitreous by laser pulses.

In a composition for the use in accordance with embodiments of the present invention, the vitreous floater being treated may have a length in the range of 1 mm to 3 mm, embodiments of the present invention not necessarily being limited thereto.

In a composition for the use in accordance with embodiments of the present invention, the vitreous floater being treated may be close to the retina or to the lens, e.g. at a distance in the range of 0 mm to 5 mm. For example, the floater may be present in the bursa premacularis. However, embodiments of the present invention are not necessarily limited to treating vitreous floaters that are close to the retina or eye lens.

In a composition for the use in accordance with embodiments of the present invention, the laser pulses may consist of one to 100 laser pulses, e.g. one to 20 laser pulses, per floater.

In a composition for the use in accordance with embodiments of the present invention, the laser pulses may have a length in the range of 10 fs to 1000 nl, for instance 10 fs to 10 ns, e.g. in the range of 10 fs to 1 ps or in the range of 1 ps to 10 ns.

In a composition for the use in accordance with embodiments of the present invention, the laser pulses may each have a power density in the range of $10^7$ to $10^{15}$ W/cm$^2$, e.g. in the range of $10^{12}$ to $10^{15}$ W/cm$^2$, or alternatively expressed a fluence in the range of 10 µJ/cm$^2$ to 100 J/cm$^2$, e.g. in the range 10 mJ/cm$^2$ to 10 J/cm$^2$.

In the examples hereinbelow, for illustrating embodiments of the present invention, compositions comprising 70-80 nm gold nanoparticles (AuNP) and 10 nm gold nanoparticles are discussed. The nanoparticles were synthesized using the processes as detailed in exemplary embodiments provided hereinabove. After synthesis, the particles were functionalized with HA or PDDAC, to obtain respectively anionic and cationic coatings, as described hereinabove.

Figure 5:
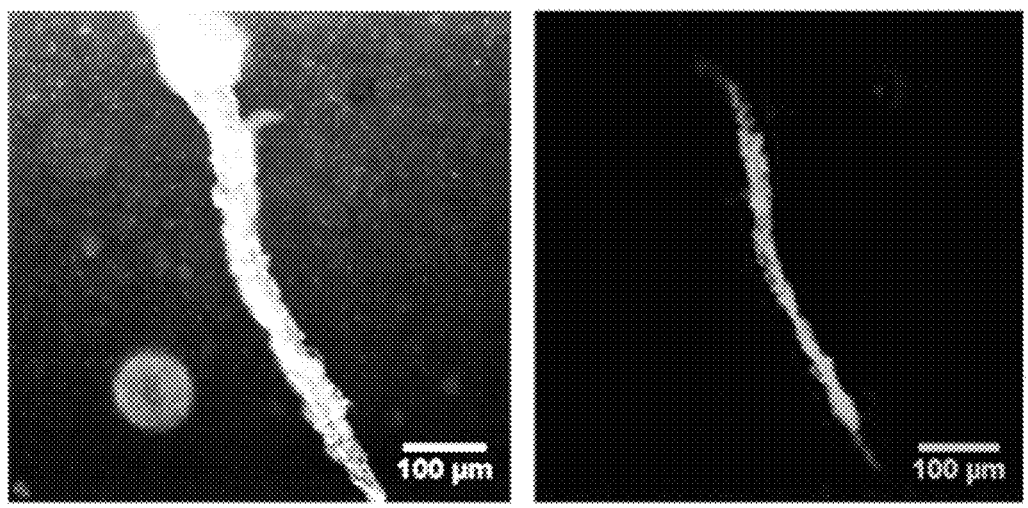
FIG. 5 shows a dark field microscopy image and a corresponding fluorescence image of a type I collagen fiber used as floater model in an example demonstrating aspects of embodiments of the present invention.

In the examples hereinbelow, collagen aggregates were used as a model for floaters. To ensure that the prepared fibers were made up of collagen and to avoid confusion with dust or any other materials during dark field microscopic imaging, the fibers were stained with Col-F, a fluorescent probe able to stain collagen and elastin. FIG. 5 shows a dark field microscopy image (left) and a corresponding fluorescence image of a collagen fiber used as floater model.

Figure 6:
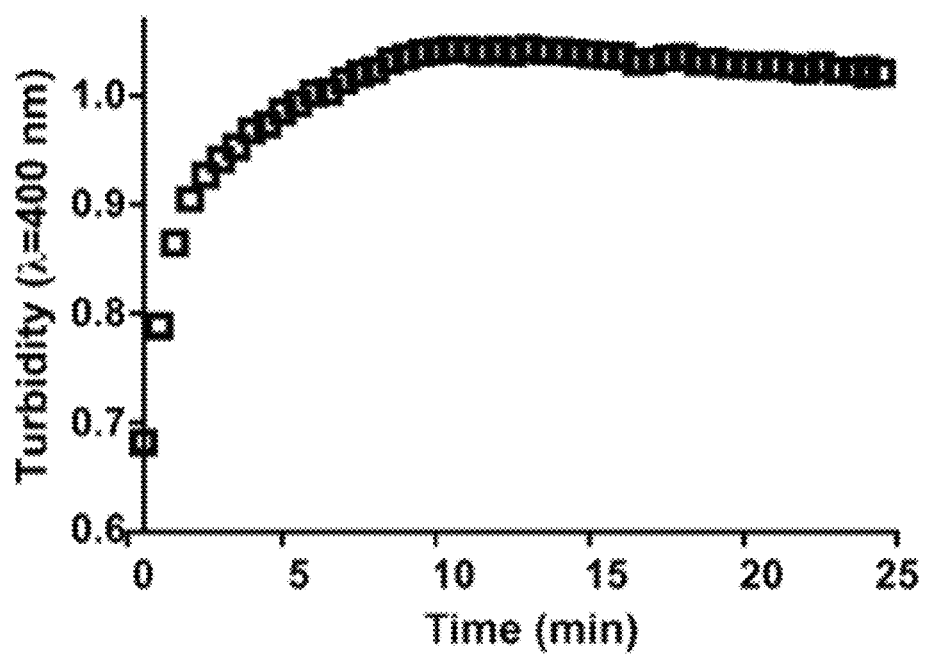
FIG. 6 shows turbidity measurements during fibrillation of a floater model, in an example demonstrating aspects of embodiments of the present invention.
Figure 8:
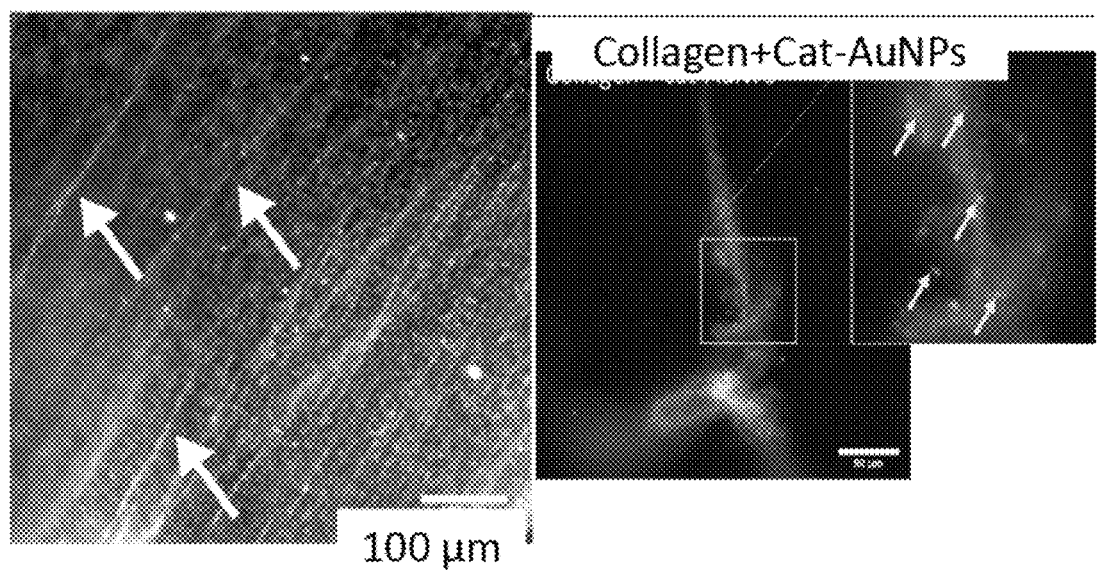
FIG. 8 demonstrates lines formed in bovine vitreous by the visualization of cationic coated gold nanoparticles bound to collagen at the left, as well as bound in collagen fibers in water on the images at the right, in an example demonstrating aspects of embodiments of the present invention.

Collagen I was extracted from rat tail (GIBCO) and diluted in PBS (0.2 mg/ml). The pH was adjusted to 7.4, using NaOH (0.1N), and the suspension was incubated at 37° C. for one hour. To monitor the fibrillation process, turbidity measurements were performed, illustrated in FIG. 6, measuring the absorbance of the collagen suspension ($\lambda$=400 nm) at 37° C. using a NanoDrop 2000c spectrophotometer (NanoDrop Technologies, Wilmington DE). The collagen solution turned turbid upon heating at 37° C., indicating the formation of collagen fibers. These fibers in water were subsequently labeled with Col-F, a fluorescent probe which stains collagen and elastin. The presence of collagen fibers could be confirmed by dark field and fluorescence microscopy, an example of which is given in FIG. 5. As the dark field microscopy images at the right in FIG. 8 show, cat-AuNPs of 70 nm spontaneously bound to the collagen fibers.

Nanoparticle tracking analysis (NTA) measurements were performed using a Nanosight instrument (Malvern, Worcestershire, UK). The cationic AuNPs were diluted in water ($10^{10}$ particles/ml) and injected with a sterile syringe in the sample chamber. Measurements were made in scattering mode. All measurements were performed at room temperature.

Yellow-green fluorescent carboxylate polystyrene nanobeads (500 nm) (Invitrogen, Merelbeke, Belgium) were mixed with 70 nm cationic gold nanoparticles (c=2.10$^{10}$ particles/ml). and injected in the vitreous by a sterile syringe with a 30 G needle. The concentration of the fluorescent nanoparticles was suitable for SPT experiments ($10^9$ particles/ml). After 30 min of equilibration time, the sample was irradiated with a nanosecond laser and films were recorded in and outside the illuminated area. For each condition, 10 to 20 movies were recorded, comprising 100 frames each. The movies were analysed using an in-house developed software.

Dark field microscopy imaging can be used to locate and align the nanosecond laser on the collagen fibers or human vitreous opacities in the sample. To generate vapor nanobubbles, 7 ns laser pulses were used. The wavelength of the laser light was 561 nm which falls within the plasmon peak of 70-80 nm AuNPs. A beam expander (#GBE05-A, Thorlabs) combined with iris diaphragm (#D37SZ, Thorlabs) was used to adjust the diameter of the laser beam to 150 µm. The laser pulse energy was monitored by an energy meter (J-25 MB-HE&LE, Energy Max-USB/RS sensors, Coherent) synchronized with the pulsed-laser. The length of the collagen fibers was determined from the microscopy images using ImageJ software.

Highly concentrated suspension of AuNPs in water or after injection in bovine vitreous were irradiated using a nanosecond laser (at an intensity of 200 µJ). 5 µL of AuNPs suspension was placed on a microscopy slide in a single particle tracking (SPT) sticker. Samples were then laser-irradiated as explained above. Time series of pictures, i.e. films, were recorded (for 566 sec). Scattering recovery in the illuminated area was measured in a region of interest superimposed with the laser beam using NIS software.

Figure 7:
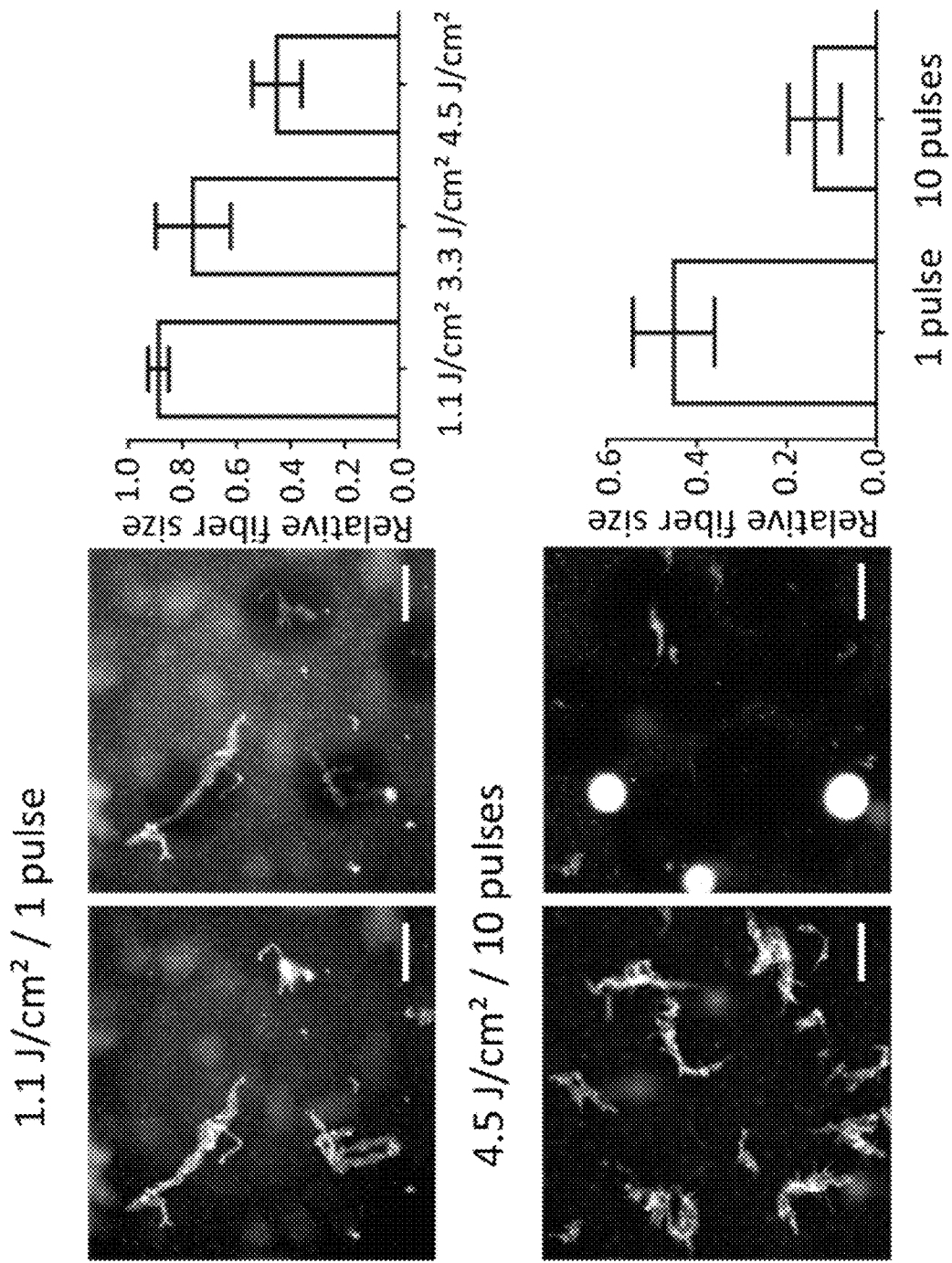
FIG. 7 shows dark field microscopy images and a diameter analysis of floater model fibers for different laser irradiation intensities and different number of pulses, in an example demonstrating aspects of embodiments of the present invention.

The cationic gold nanoparticles of diameter of 70 nm (Cat-AuNPs) were mixed with the collagen fibers in water. The suspension was exposed to the nanosecond laser at different intensities with a different number of pulses. The laser beam was focused on the center of the targeted fiber. Fiber diameters before and after laser exposure were determined and averaged using the ImageJ image manipulation software. FIG. 7 shows, in the leftmost column, dark field microscopy images and, in the second column, fluorescence microscopy images. The third and rightmost column in FIG. 7 shows the results of the diameter analysis using the ImageJ software. Referring to the top row in FIG. 7, no effects were observed for an intensity of 200 µJ (around 1.1 J/cm$^2$) on the fiber diameter. Referring to the bottom row in FIG. 7, for an intensity of 800 µJ (around 4.5 J/cm$^2$), it became clear that the size of the fiber was reduced after exposure. Ten pulses at 800 µJ (around 4.5 J/cm$^2$) were required to destroy most of the fibers. This experiment clearly demonstrates the use of a composition comprising particles in accordance with embodiments of the present invention in a laser irradiation therapy, e.g. using a pulsed laser, can be used for treating eye floaters.

To demonstrate the impact of vapor nanobubble (VNB) formation by the irradiated Cat-AuNPs on the bovine vitreous, e.g. in terms of the intactness of the vitreous network and the viscosity, single particle tracking (SPT) experiments were carried out outside and in the area where the laser beam meets the vitreous. Carboxylic-terminated fluorescent polystyrene nanospheres (PS COOH nanoparticles) with a size of 500 nm were tracked and used as a viscosity sensor. These nanoparticles can be considered to be substantially immobile in the vitreous due to hydrophobic interactions and steric effects and due to their size being close to the lattice size of the vitreous mesh (about 550 nm). For this example, 70 nm Cat-AuNPs were used. It can be observed that lines are formed after injection in the bovine vitreous, which provides a clear indication on their interaction with the vitreous network, as shown in FIG. 8. Moreover, these particles sufficiently scattered light to be detectable in the experiment, such that a clear visualization of the illuminated area over time is obtained.

Figure 9:
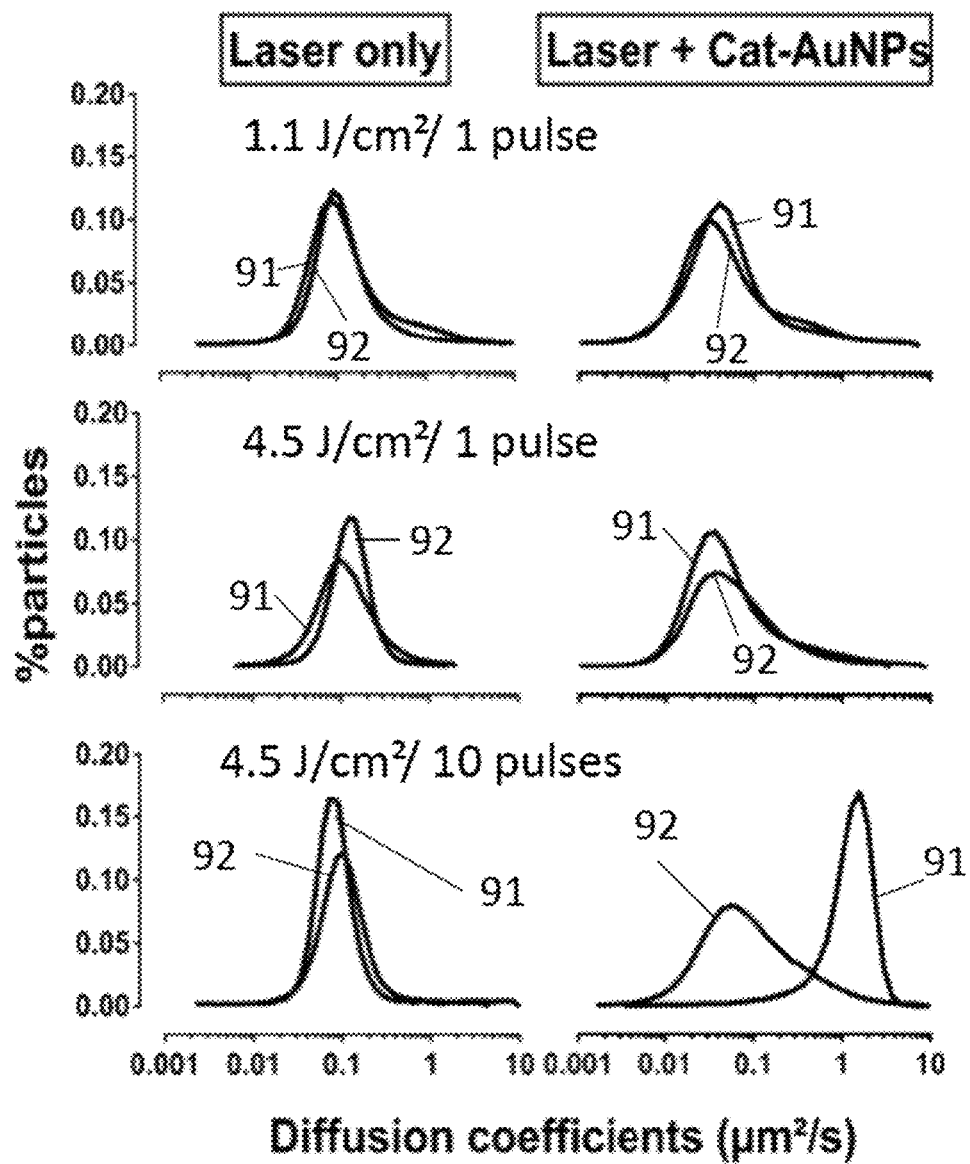
FIG. 9 shows changes in diffusion of particles after irradiation, in an example demonstrating aspects of embodiments of the present invention.
Figure 10:
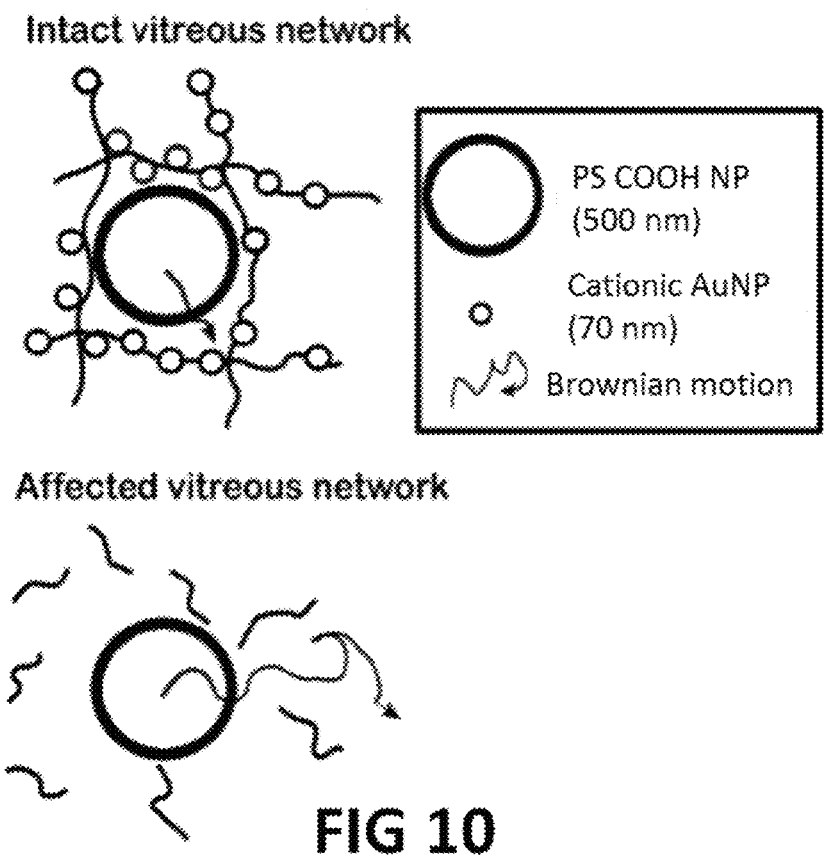
FIG. 10 schematically illustrates a local destruction of the vitreous meshwork where cationic coated gold particles bind to the vitreous collagen network, in an example demonstrating aspects of embodiments of the present invention.

To evaluate the local impact of VNBs generation on the vitreous, the laser intensities that were used to break and/or move floaters in the example provided hereinabove, in water, were retained (i.e. 200 µJ (around 1.1 J/cm$^2$) and 800 µJ (around 4.5 J/cm$^2$). Application of the laser in the absence of the Cat-AuNPs did not induce any significant changes in the diffusion of the PS COOH nanoparticles. In the presence of Cat-AuNPs, one pulse at a laser intensity of 200 µJ (around 1.1 J/cm$^2$) or 800 µJ (around 4.5 J/cm$^2$) did not cause a clear observable change in diffusion, whereas 10 pulses at an intensity of 800 µJ (around 4.5 J/cm$^2$) led to a clear increase in the diffusion coefficient of COOH PS nanoparticles (see FIG. 9). In FIG. 9, the curves 91 represent the distribution of the diffusion coefficient as measured in an area where the laser irradiates the vitreous, while the curves 92 are acquired in an area that is remote from the illuminated area to act as control. This can be explained by a local destruction of the vitreous meshwork where cationic AuNPs bind, as schematically illustrated in FIG. 10. COOH PS nanoparticles that were trapped in the vitreous meshwork can move freely after laser-induced liquefaction of the vitreous meshwork. This local liquefaction can be attributed to VNB generation where the Cat-AuNPs clustered to vitreous components (e.g. to hyaluronic acid, proteoglycans and/or collagen), since no comparable effect was observed when applying the laser in the absence of the Cat-AuNPs to the vitreous.

For example, local liquefaction around an eye floater may be useful to sediment floater residuals out of the field of view. This phenomenon is also observed with substantially higher laser intensities in a conventional prior-art therapy that uses the clinically-approved Nd:YAG laser, e.g. particularly when applied in the mid- and posterior vitreous humor.

It is an advantage of a composition comprising gold nanoparticles coated with HA, e.g. particularly smaller particles, that destruction of the vitreous mesh could be reduced, since these particles may not generate VNBs with such high intensity. For example, anionic hydrophilic particles having a small diameter may be more mobile in the vitreous network than the exemplary Cat-AuNPs described hereinabove, e.g. due to their smaller size and negative charge, which may imply smaller and/or less interactions with the collagen network.

The mobility of macromolecules and nanoparticles after intravitreal injection is clearly correlated to their size and their surface charge. These phenomena have a direct implication in ocular drug delivery. While cationic particles may aggregate at the injection spot in the vitreous, anionic particles may have a higher mobility. Different types of nanoparticles coated with poly(ethylene)glycol (PEG) or hyaluronic acid (HA) showed enhanced mobility and diffusion coefficient in vitreous when compared to non-coated particles. To break floater-causing vitreous opacities, the particles may need to be sufficiently mobile in the vitreous body to increase the probability of binding to vitreous opacities after injection and to avoid aggregation at the injection spot. While a potent destruction of the surrounding vitreous network with cationic particles, e.g. the Cat-AuNPs of the example hereinabove, may have useful medical applications in (locally) liquefying the vitreous, for other applications, such as inducing prophylactic post vitreous detachment (PVD) while for attempting to preserve the vitreous mesh, anionic particles, and particularly smaller sizes of anionic particles, may be preferable.

To examine whether particles can reach the floaters efficiently and to evaluate the impact of the particle coating on their mobility, a technique inspired from fluorescence recovery after photobleaching (FRAP) has been used in the following example. FRAP is a powerful tool to study the mobility of fluorescent particles or molecules in different media.

For SRAF mobility experiments in water, 5 µL of AuNPs suspension ($10^{12}$ particles/ml in water) was placed on a microscopy slide. For measuring the mobility of the AuNPs in the vitreous through SRAF, 40 µL of a highly concentrated suspension of AuNPs (typically $10^{12}$ particles/ml in water) was injected in a bovine vitreous sample (200-400 µl) contained in a glass-bottomed dish and allowed to equilibrate for 30 min. Then samples were placed under the dark field microscope (10× objective) and illuminated with the nanosecond laser (Opolette HE 355 LD, OPOTEK Inc; 561 nm; 200 µJ (around 1.1 J/cm$^2$); 1 pulse) to fragment the AuNPs; subsequently the increased intensity of scattered light in the fragmentation zone was recorded for about 10 min.

Figure 11:
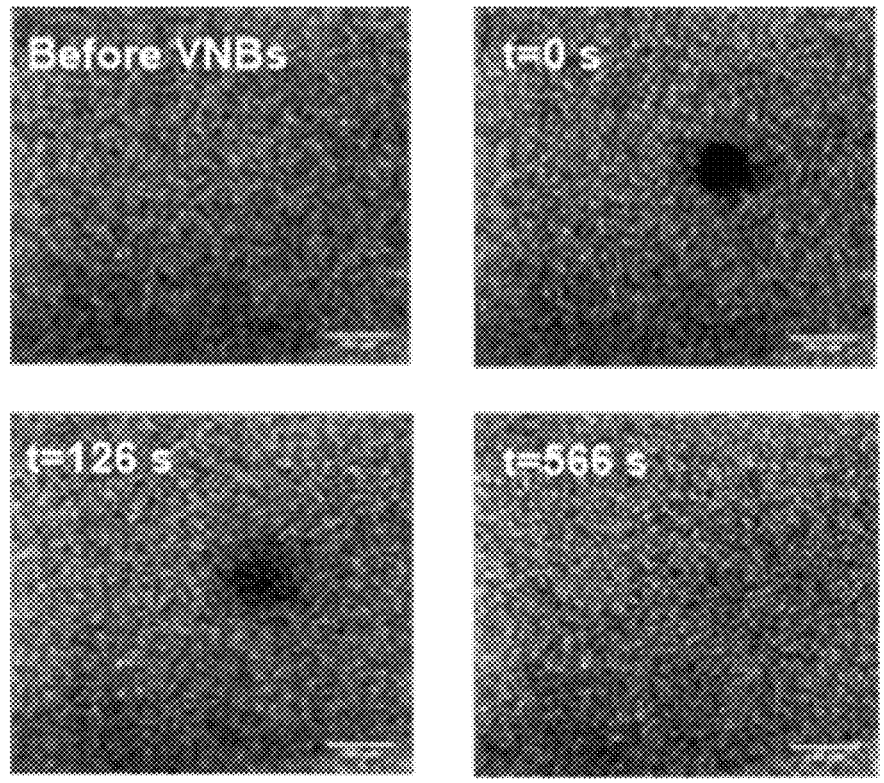
FIG. 11 shows representative images of scattering recovery of hyaluronic acid coated gold nanoparticles in water before, during and after laser-induced vapor nanobubble formation

The applied technique is based on scattering recovery in an area where AuNPs were illuminated and destroyed by the nanosecond laser and imaged by dark-field microscopy without any fluorescent staining. This technique allows to determine the mobility of AuNPs without any fluorescent staining and offers an alternative to techniques such as NTA, which may affect vitreous integrity due to shear stress during injection. After a single laser pulse of 200 µJ (around 1.1 J/cm$^2$) intensity, a hole is created. In this area, the scattering recovery of AuNPs can be measured and plotted as a function of time. FIG. 11 shows representative images of scattering recovery of HA-AuNPs in water before, during (t=0 s) and after VNBs generation.

The diffusion coefficient D [µm$^2$/s] can be determined by $$D = \frac{w^2}{4\tau},$$

where w [µm] refers to the radius of the laser beam and τ [s] refers to a half-life factor. The mobility k can be determined by the value of relative fluorescence intensity corresponding to the plateau.

Figure 12:
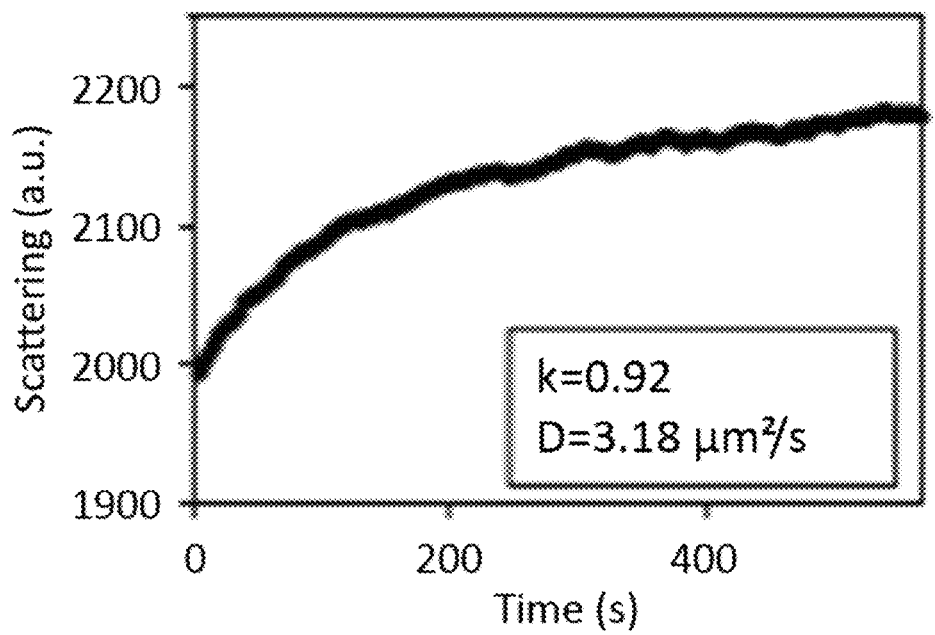
FIG. 12 shows the diffusion coefficient and mobility of hyaluronic acid coated gold nanoparticles in water.
Figure 13:
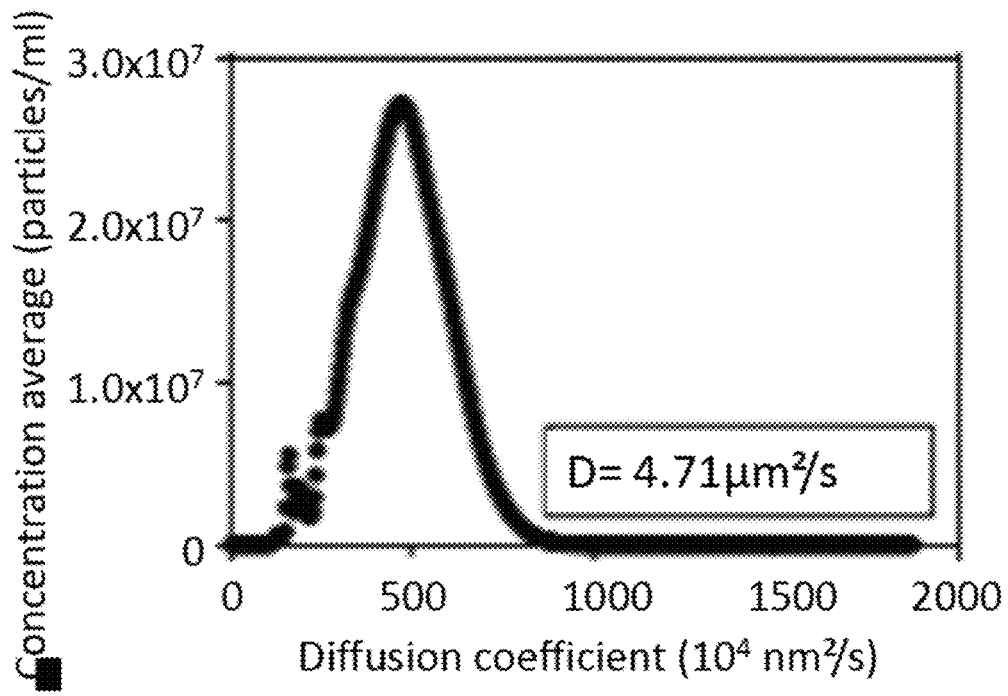
FIG. 13 shows a diffusion coefficient distribution of hyaluronic acid coated gold nanoparticles estimated by nanoparticle tracking analysis (NTA).

The diffusion coefficient (D) and mobility (k) of HA-AuNPs (c=3.2×10$^{10}$ particles/ml) in water were found to be around 3.18+/−0.07 µm$^2$/s and 0.92+/−0.07 respectively, see FIG. 12. Values of the diffusion coefficient obtained with this technique can be compared to values of the diffusion coefficient obtained by nanoparticle tracking analysis (NTA), which gave a value of 4.71+/−0.77 µm$^2$/s, i.e. of the same order of magnitude, see FIG. 13.

Figure 14:
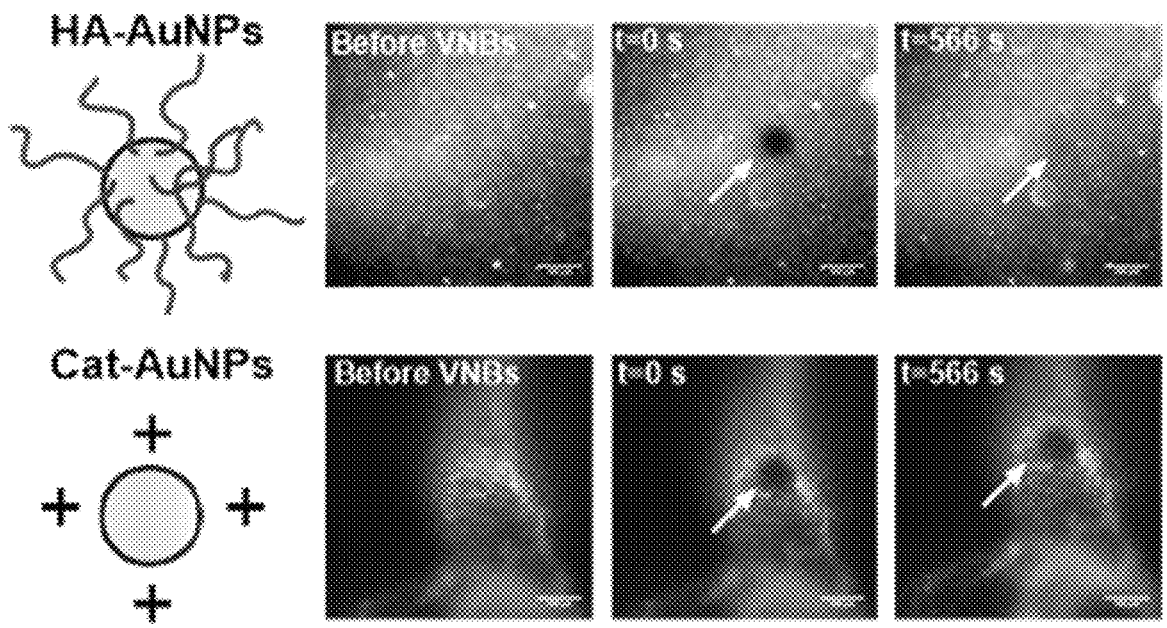
FIG. 14 shows a low diffusion of cationic-coated particles in bovine vitreous.
Figure 15:
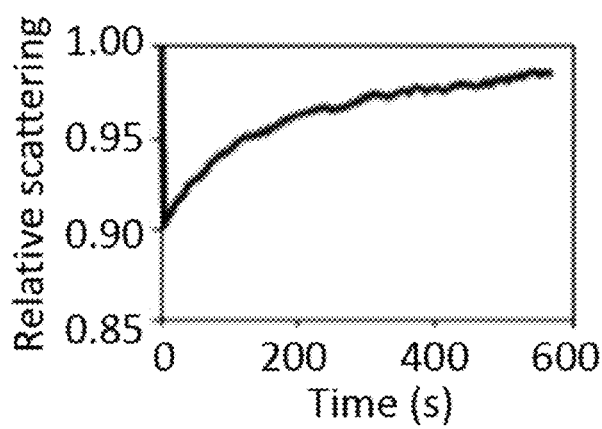
FIG. 15 shows scattering recovery in the area where hyaluronic acid coated gold nanoparticles in vitreous were irradiated.
Figure 16:
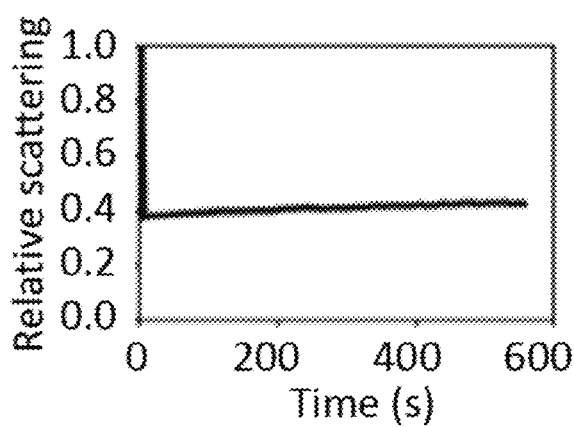
FIG. 16 shows no observable scattering recovery in the area where cationic-coated gold nanoparticles in vitreous were irradiated.

HA-AuNPs were shown to be mobile in water and bovine vitreous (k=0.99) but having a decreased diffusion coefficient D in bovine vitreous (D=1.86+/−0.40 µm$^2$/s). However, Cat-AuNPs substantially remained at the injection spot in the vitreous, e.g. as shown by the images in FIG. 14. FIG. 14 shows the outcome of SRAF measurements on respectively cat-AuNPs and HA-AuNPs injected in bovine vitreous. No scattering recovery was observed in the area where AuNPs were illuminated, see FIG. 14 bottom and FIG. 16. This indicates a poor or no mobility of the Cat-AuNPs in the vitreous. However, HA-AuNPs showed scattering recovery in the bovine vitreous, with a diffusion coefficient (1.9+/−0.4

µm²/s) somewhat lower than in water, as could be expected due to the presence of the biopolymer network in the vitreous, confirming a mobility-facilitating role of hyaluronic acid in the vitreous, see FIG. 14 top and FIG. 15.

Figure 17:
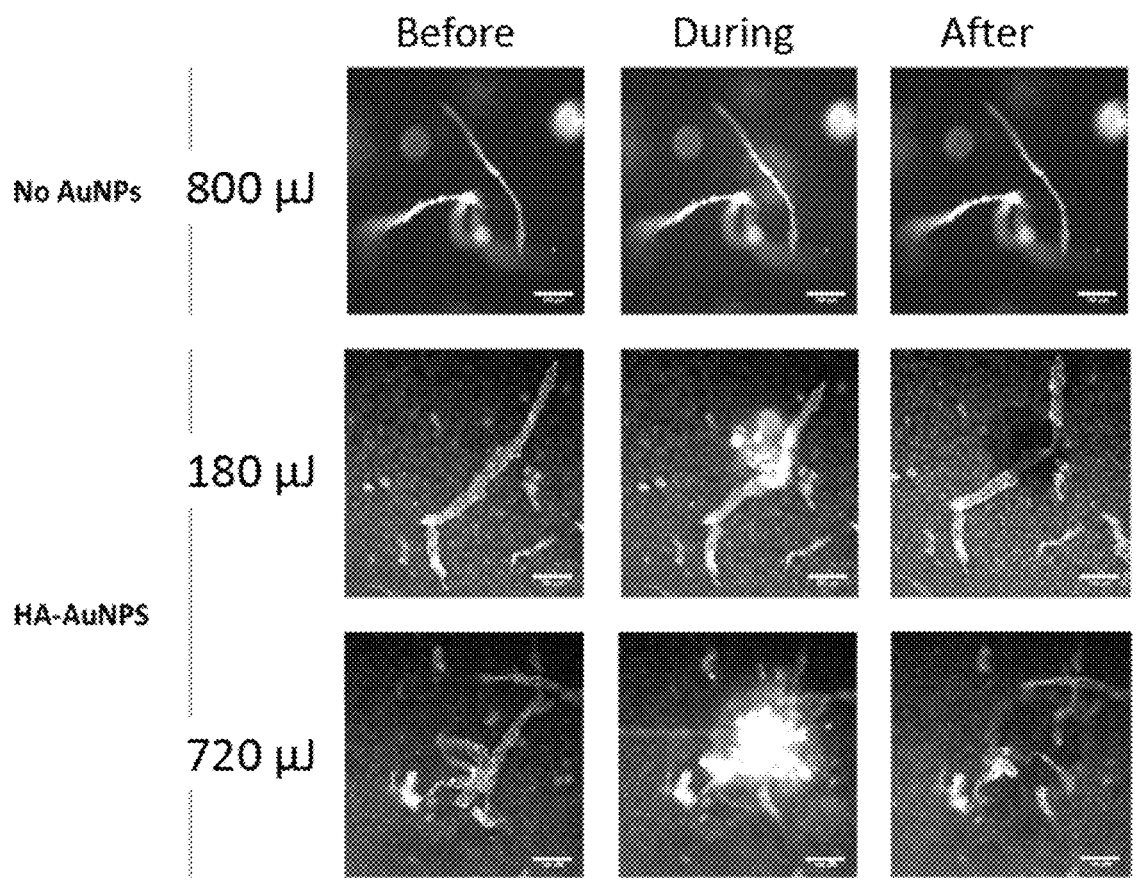
FIG. 17 demonstrates the capacity of hyaluronic acid coated gold nanoparticles, having a diameter of 80 nm, to generate vapor nanobubble upon laser exposure.

Referring to FIG. 17, in the following example, HA-AuNPs of a size of 70 nm were mixed with collagen I fibers. The capacity of HA-AuNPs to generate VNBs upon laser exposure was confirmed. As discussed hereinabove, no VNBs are observed and collagen fibers are not observably affected in the absence of HA-AuNPs at a laser intensity of 800 µJ (around 4.5 J/cm²). However, illumination by the nanosecond laser shows a breakage and/or folding of the fibers, depending on the laser intensity, in the presence of AuNPs. With a laser intensity of 200 µJ (around 1.1 J/cm²), collagen fibers were poorly affected but moved over a short distance or folded, analogous to the example hereinabove with Cat-AuNPs. When the laser intensity was increased up to 800 µJ (around 4.5 J/cm²), fibers were clearly broken into several fragments, confirming the previous observations with Cat-AuNPs (see FIG. 7).

Figure 18:
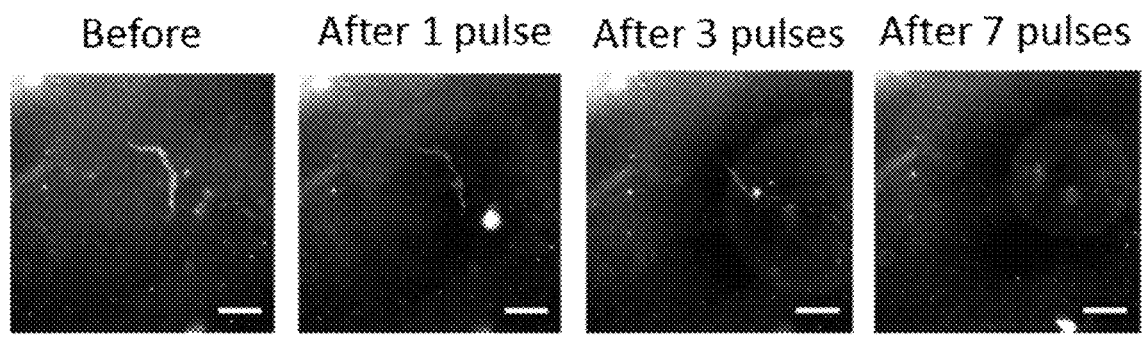
FIG. 18 shows dark-field microscopy images of a type I collagen fiber after different numbers of laser pulses at a laser intensity of 4.5 J/cm$^2$, for hyaluronic acid coated gold nanoparticles interacting with collagen fibers in bovine vitreous.

The same experiment was carried out by injecting the collagen fibers in bovine vitreous. After 30 min, HA-AuNPs were injected at several locations with a maximum volume of 40 µL (to avoid local liquefaction of the vitreous due to the injection). Dark-field microscopy images of a collagen fiber showed breakage at a laser intensity of 800 µJ (around 4.5 J/cm²), confirming previous observations in water and a complete disappearance of the fiber after 7 pulses, see FIG. 18. These observations emphasize the capacity of HA-coated AuNPs to interact with, e.g. specifically bind to, collagen fibers. Thus, HA-coated particles that are negatively charged produced similar breakage as Cat-AuNPs.

Figure 19:
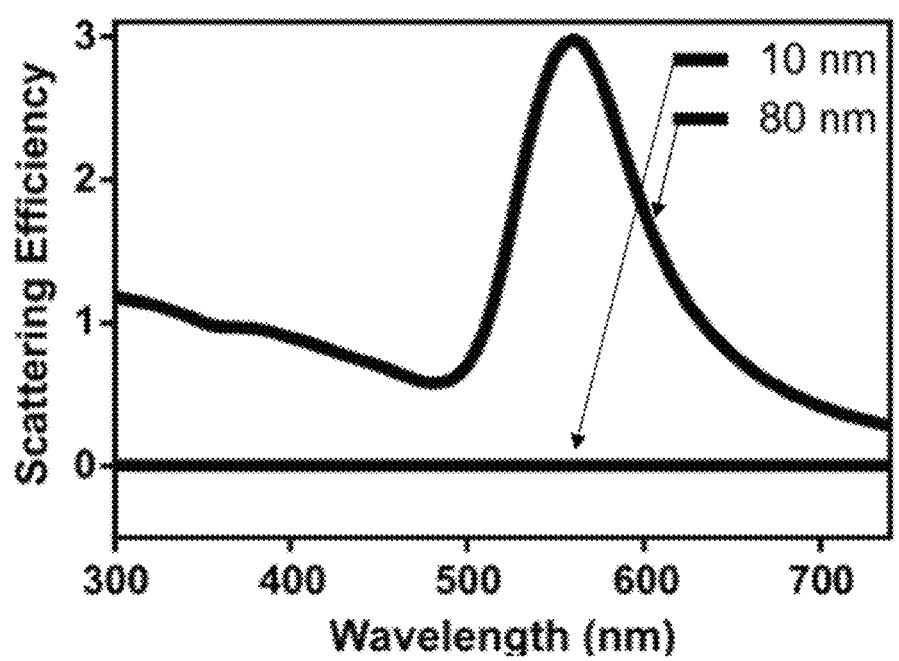
FIG. 19 shows simulated scattering of hyaluronic acid coated gold nanoparticles having a diameter of respectively 10 nm and 80 nm.
Figure 20:
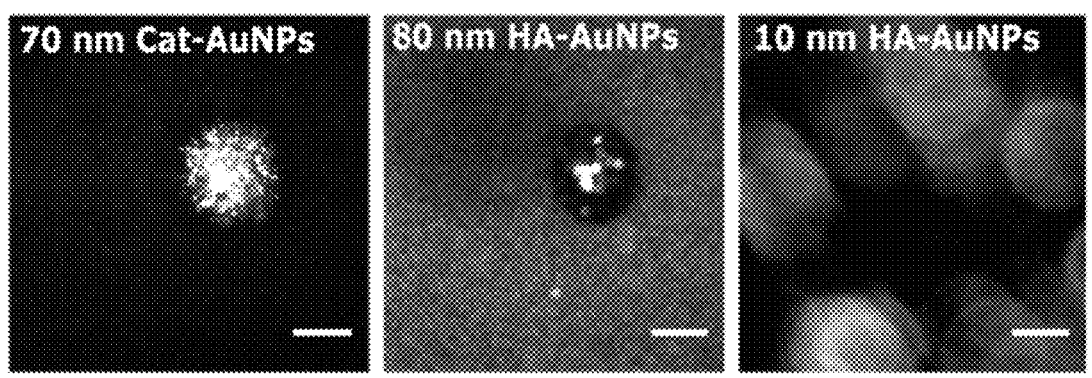
FIG. 20 shows that for a laser irradiation intensity of 1.1 J/cm$^2$, vapor nanobubbles can be formed by irradiation of cationic-coated gold nanoparticles and hyaluronic acid coated gold nanoparticles of respectively diameters of 70 and 80 nm, but not by 10 nm hyaluronic acid coated gold nanoparticles in water.

Scattering efficiency may be an important criterion for the use of AuNPs intravitreally. Depending on the shape of the particles (e.g. spheres, rods . . . ) and size, AuNPs can scatter light to a different extent. Scattering may be generally considered as undesirable because the patient may experience a decrease in visual acuity or a blurred vision after injection. The examples hereinabove have demonstrated a good mobility in the vitreous for hyaluronan-coated particles. In this example, HA-coated AuNPs of a size of 10 nm were synthesized and their ability to break collagen fibers in water and bovine vitreous were studied. For a smaller size of 10 nm, simulated scattering efficiency substantially showed no scattering as compared to 80 nm AuNPs, see e.g. FIG. 19 (for further reference, simulation details are explained in the annex 1). Furthermore, the threshold to generate VNBs with 10 nm AuNPs is higher than for 70 or 80 nm nanoparticles. For an intensity of 200 µJ (around 1.1 J/cm²), it is clear that VNBs can be observed with both Cat-AuNPs and HA-AuNPs (70 and 80 nm respectively) but not with 10 nm HA-AuNPs (see FIG. 20). The absence of background due to low scattering can be noted as well. However, 10 nm AuNPs can easily generate VNBs after clustering and may thus generate bubbles when aggregated on a collagen fiber. This may advantageously avoid or reduce potent collateral damage to the vitreous lattice with unbound particles as seen in an example hereinabove for Cat-AuNPs, and may, surprisingly, provide a specific targeting of the floater while protecting the vitreous lattice from substantial damage. It is to be noted that this effect may extend over a wider range of particle sizes, e.g. in the range of 1 nm to 50 nm, or in the range of 1 nm to 20 nm, or in the range of 1 nm to 10 nm. It is also to be noted that this effect may also be observed for different types of cores, e.g. silver, platinum, polymer, carbon and the like, since the properties of the core might have only a small influence on the mobility, binding and scattering properties. It is also to be noted that this effect may extend to different types of coating, e.g. to similar anionic hydrophilic coatings.

The number of VNBs generated per laser pulse was determined by dark-field microscopy. Dispersions of HA-AuNPs in water ($10^{10}$ nanoparticles/mL) were applied in a 50 mm glass bottom dish (MatTek Corporation, US). After an equilibration of 1 hour, a single 7 ns laser pulse was applied and the number of VNBs were counted in the irradiated area (~150 µm laser beam diameter) of the dark field images. Dark field images were recorded with an illumination time of 10 ms after firing the laser pulse so as to capture the short-lived VNBs. As the laser fluence (i.e. the energy density calculated as the energy of a single laser pulse divided by the laser beam area), increases, more AuNPs in the irradiated zone will form VNBs.

In water and in bovine vitreous, 10 nm HA-AuNPs ($1.10^{12}$ particles/ml) were shown to induce fiber breakage at a laser intensity of 800 µJ (around 4.5 J/cm²) (see FIG. 21) after 1 pulse. However, the required particle concentration to break the fibers was higher than what was observed for the larger AuNPs. This may be due to the higher threshold to generate VNBs that must be reached for small AuNPs. After 7 pulses with an energy of 800 µJ (around 4.5 J/cm²), the fiber is no longer observable in the bovine vitreous. It may be noted that the AuNPs are preferably injected close to the floater to see an effect. It is also important to consider the location of the floater. For example, the required number of pulses may vary when the floater is located deeper, similar to what has been observed in the art for conventional Nd:YAG laser treatments when the floater is located in the posterior segment of the vitreous.

Transmission electron microscopy (TEM) images were obtained at the VIB-UGent Transmission Electron Microscopy-Core facility using a JEM-JEOL 1120 EXII under an accelerating voltage of 80 kV. Samples were prepared by adding one drop (of about 50 µL) of the colloidal solutions onto a holey carbon-formvar coated copper TEM grid (100 mesh).

Figure 22:
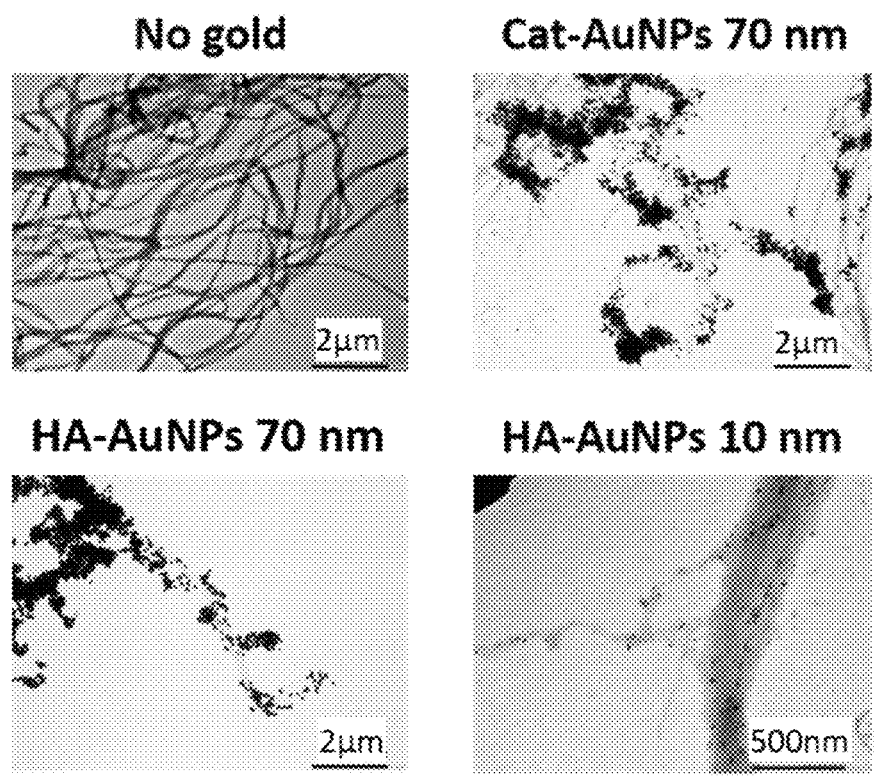
FIG. 22 shows transmission electron microscopy images of particles binding to collagen structures.

Observations of particles and collagen fibers by TEM reveals that all types of particles as discussed in the examples hereinabove can bind collagen structures, regardless their size and charge, see FIG. 22. This result confirms that such particles, e.g. AuNPs, can be used to destroy eye floaters or vitreous opacities. Gold may be a particularly suitable core material for the particles, due to the binding of gold to collagen, e.g. due to the presence of both anionic sites and amine groups on the surface of collagen fibrils. TEM observations confirmed the interaction of AuNPs and collagen structures that was assumed based on the dark-field microscopic imaging (e.g. the "granular" aspect of the fibers in the presence of gold) and with the naked eye (a "reddish" tint of the fibers in the presence of gold).

Figure 24:
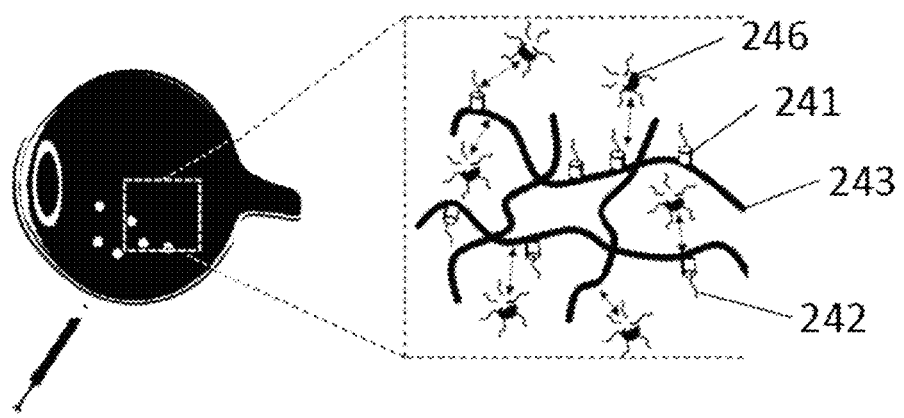
FIG. 24 shows schematically the repulsion between HA-AuNPs in vitreous.

Without being bound by theory, it is believed that the nanoparticles provided by aspects of the present invention can move through the vitreous but attach to vitreous opacity because of the differences in the structure of the opacity. More specifically, nanoparticle mobility in vitreous can be improved by applying a HA coating to the nanoparticles. In particular, coating Au nanoparticles with HA avoids their immobilization in vitreous. As shown in FIG. 24, the collagen strands 243 ('fibrils') in the biopolymer network of the vitreous are likely connected to HA (mediated by glycosaminoglycans (GAGs) such as chondroitin sulfates 241, shown in FIG. 24). The negatively charged HA 242 on the collagen strands 243 keep the strands sufficiently apart. This minimizes light scattering, keeping the vitreous transparent. As schematically presented in FIG. 24, electrostatic repulsions may therefore possibly occur between HA-AuNPs 246 and HA connected to the collagen strands, explaining why HA-AuNPs remain mobile in vitreous. Instead, cationic AuNPs likely bind to the negatively charged HA molecules, causing immobilization to the collagen strands.

Figure 23:
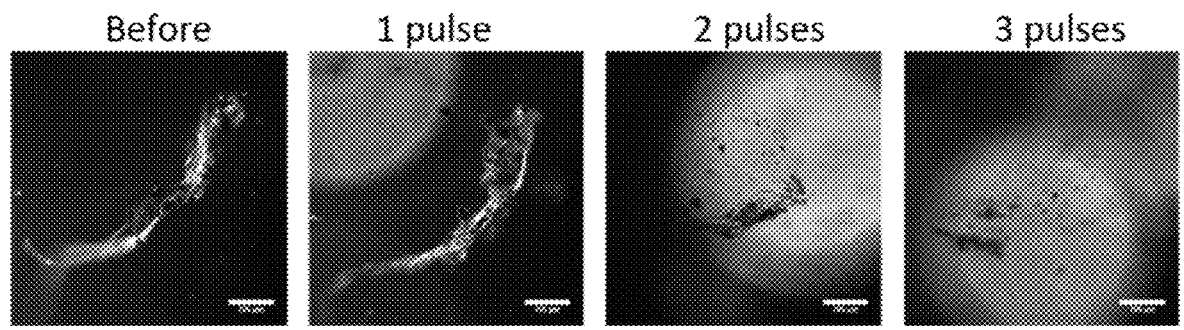
FIG. 23 shows dark-field microscopy images of a large human floater treated with 10 nm hyaluronic acid coated gold nanoparticles and laser-irradiated at a laser intensity of 4.5 J/cm$^2$.
Figure 25:
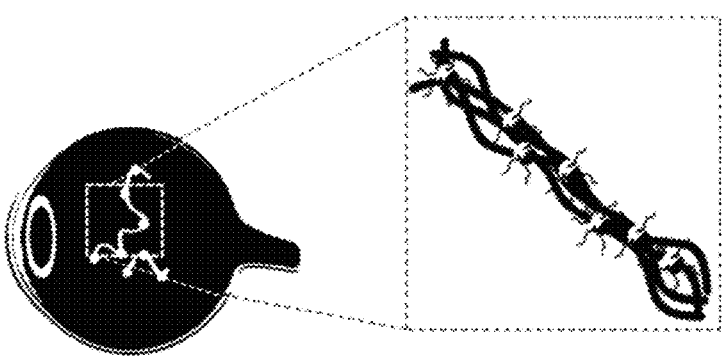
FIG. 25 shows schematically the binding of HA-AuNPs to a vitreous opacity.
Figure 26:
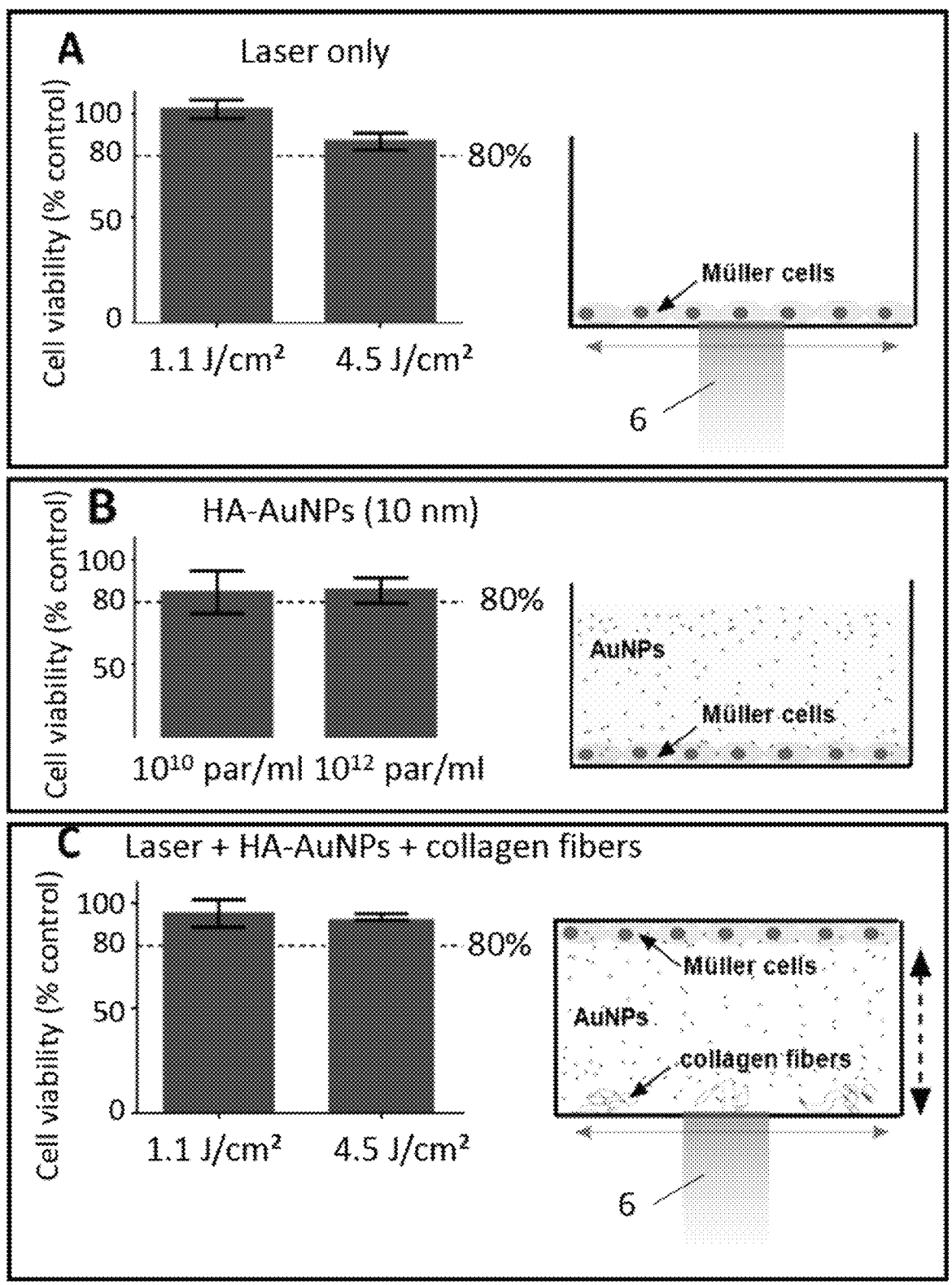
FIG. 26 shows MTT assay of cell viability of immortalized Muller cells 24 h after exposing the cells to the pulsed-laser only (A), after treating the cells with 10 nm HA-AuNPs only (without applying laser light) (B), and Muller cells located at a distance of 10 mm from collagen fibers; the cells were first exposed to 10 nm HA-AuNPs (1012 particles/ml) for 24 h; subsequently the layer of collagen fibers was scanned (single scan) through a laser beam.

Surprisingly, while the negatively charged HA-AuNPs do not seem to interact with the collagen strands of the biopolymer network in vitreous, they do bind to type I collagen fibers (see e.g. FIG. 17) and human vitreous opacities (FIG. 23), similar to what was observed for cationic AuNPs (FIG. 7). As vitreous opacities are often present in liquefied parts of the vitreous, one can assume that HA is absent on the surface of the opacities or, at least, present in a lower concentration in their immediate surroundings. This absence of HA (and thus absence of electrostatic interactions) might explain why HA-AuNPs keep their binding capacity to opacities, as schematically illustrated in FIG. 25. Thus, the HA provides mobility in the vitreous by providing repulsion from the collagen strands linked to HA, while it provides binding to opacities by attractive forces between the HA of the coating of the nanoparticles and the HA-depleted fibril.

For a concentration of $10^{10}$ particles/ml, no aggregation is observed on the collagen fiber with 10 nm HA-AuNPs, which may explain why no breaking or other effect was observed on the collagen fiber at this concentration in examples hereinabove for these particles. However, for larger particles, it was possible to break the fibers at this concentration due to a lower threshold to trigger VNBs.

Figure 21:
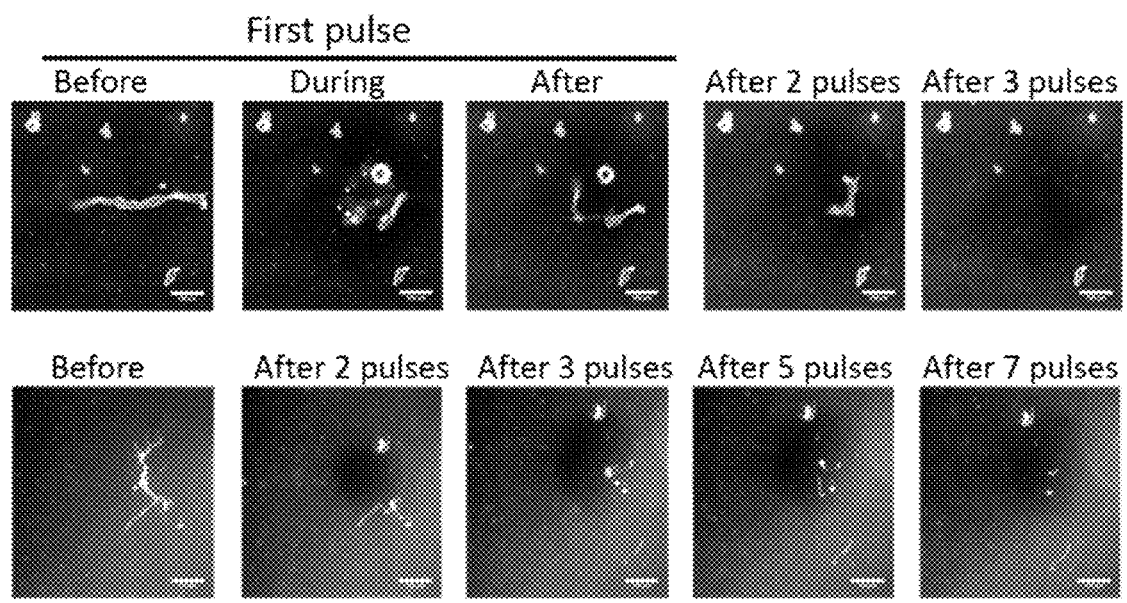
FIG. 21 shows collagen fiber breakage using 10 nm hyaluronic acid coated gold nanoparticles irradiated at a laser intensity of 4.5 J/cm$^2$ after several pulses in water and bovine vitreous.

Because the composition of human floater-causing opacities may be more complex than the models discussed hereinabove, the example hereinbelow was carried out in human vitreous containing floater-causing opacities. These vitreous were obtained by pars plana vitrectomy. Samples of vitreous containing floaters were collected at the VMR institute after vitrectomy of patients. FIG. 21 shows darkfield microscopy images of a large human floater treated with 10 nm HA-AuNPs ($10^{12}$ particles/ml) and at a laser intensity of 4.5 J/cm$^2$. The sample was mixed with a colloidal suspension of gold (1:1 vol/vol). It is observed that human floaters can be destroyed in the same way and similar parameters (4.5 J/cm$^2$ and 10 nm HA-AuNPs, $10^{12}$ particles/ml). While small particles (e.g. 10 nm size nanoparticles) diffuse more easily through vitreous (a requirement to reach the floaters) and scatter less light which might provide more comfort to the patient, they are too small to generate VNBs for laser energies at which larger nanoparticles do produce VNBs. Importantly, however, 10 nm HA-AuNPs bind and cluster on the surface of collagen fibers which improves light absorption and lowers the laser energy required to generate nanobubbles. This allows to use laser pulses which are strong enough to generate nanobubbles on the fibers, while they are too weak to generate nanobubbles in the surroundings. This 'fiber-specific nanobubble generation' is attractive as it may minimize potential damage to the surrounding vitreous and tissues.

In traditional YAG laser vitreolysis, floaters are destroyed by plasma formation, requiring laser pulses at very high energy densities up to 5000 J/cm$^2$. Since a single YAG laser pulse typically has an energy in the order of 10 mJ, it means that the laser beam needs to be tightly focused to less than 20 μm diameter onto the floaters to achieve local photo destruction. Considering that vitreous opacities can have much larger dimensions, up to 1000 shots may be needed to destroy a single opacity, amounting to a total light dose of $10^4$ mJ.

By comparison, the present invention provides a composition comprising particles as sensitizing agent to enhance light absorption so that much lower energy densities and total light doses are needed to achieve the same effect.

In particular embodiments, the laser beam may be larger than 20 μm, for example in the order of hundred microns, e.g. the laser beam may have a diameter of 150 μm and pulses had an energy of less than 10 mJ, e.g. 1 mJ or less, e.g. 0.8 mJ. This means that the light energy density can be as low as 4.5 J/cm$^2$, which is approximately 1000 times less than what is used for YAG laser therapy. In addition, since consequently the laser beam can be much larger, fewer laser pulses are needed to completely destroy the fibers. In embodiments of the present invention, less than thousands, e.g. less than hundred pulses may be needed, for example only about 10 pulses can be used to destroy opacities, which corresponds to a total light dose of about 10 mJ, again approximately 1000 times less than YAG laser therapy. Thus, gold nanoparticle assisted photo-ablation of vitreous opacities might be less damaging for the posterior segment of the eye, as a significantly lower number of weaker laser pulses seem to be sufficient to break opacities. Another practical advantage of being able to use a larger laser beam is that the distance along the optical axis (direction of light propagation) over which a suitable energy density is achieved for photo-ablation is much larger. Indeed, assuming a Gaussian beam profile for simplicity, the depth of focus scales with the square of the beam spot size. This means that for a laser beam of 150 μm diameter, the depth of focus is at least 56 times (150 μm/20 μm)$^2$) more extended as compared to the lower than 20 μm beam for the YAG laser. In practice, this means that 3D focusing onto the floater is not such a stringent requirement, making the whole procedure much easier to perform.

Annex 1: Simulation of the Optical Properties of Gold Nanoparticles

The optical responses (i.e. scattering, absorption and extinction) of AuNPs were computed using Mie theory, which constitutes an exact solution to the problem of absorption and scattering of light by an object composed by concentric spheres. In particular, the Generalized Multiparticle Mie Theory (GMM) formulation developed by Xu (Xu, Y.; Wang, R. T. Electromagnetic Scattering by an Aggregate of Spheres: Theoretical and Experimental Study of the Amplitude Scattering Matrix. *Phys. Rev. E* 1998, 58 (3), 3931-3948) was used. This method is able to exactly solve the complex problem of interaction between an electromagnetic field and an aggregate of spheres, and was used to simulate the extinction, scattering and absorption cross sections. In all the calculations presented in this work the dielectric function tabulated by Palik for Au was employed. In the calculations performed, the nanoparticles were excited by a plane wave with an incidence pointing vector (propagation direction) normal to the surface. As the GMM code is restricted to applications in homogeneous media, an effective medium approximation was used (Chettiar, U. K.; Engheta, N. Internal Homogenization: Effective Permittivity of a Coated Sphere. *Opt. Express* 2012, 20 (21), 22976-22986) to account for the interface between the particle surface and the aqueous environment. It was considered that particles were immersed in a dielectric environment with an effective refractive index ($n_{eff}$) of 1.35, which was calculated as the weighted average of 20% of the refractive index of collagen ($n_r$ 1.41) and 80% of the refractive index of water ($n_r$ 1.33) (Leonard, D. W.; Meek, K. M. Refractive Indices of the Collagen Fibrils and Extrafibrillar Material of the Corneal Stroma. *Biophys. J.* 1997, 72 (3), 1382-1387).

Annex 2: Vitreous Samples a) Bovine Vitreous Containing Collagen I Fibers

Bovine eyes were enucleated less than one hour after cows were slaughtered (slaughterhouse Zele, Belgium). Since vitreous has a very fragile structure, it was carefully removed from the globe. First, 200 to 400 µl was carefully cut and placed on a glass-bottomed culture dish. Subsequently 50 µl of a suspension of collagen fibers was injected in the vitreous sample using a 1 ml syringe equipped with a 21.5 G needle and let to equilibrate at room temperature for 30 min. AuNPs were then randomly injected in the sample (no more than 40 µl per injection) using a 1 ml syringe equipped with a 30 G needle (no more than 5 injection spots per vitreous sample to avoid extensive liquefaction). The sample was let to equilibrate for 30 min prior to applying (nanosecond) laser pulses (Opolette HE 355 LD laser, OPOTEK Inc.)

b) Human Vitreous Containing Opacities

Samples of vitreous containing opacities were collected at the VMR Institute for Vitreous Macula Retina (Huntington beach, CA, USA) from patients undergoing vitrectomy for the treatment of Vision Degrading Myodesopsia. The study protocol adhered to the Declaration of Helsinki. Prior to surgery, patients gave a written informed consent that has been reviewed and accepted by the ethical committee of Saint Joseph Health Center for clinical research (Irvine, CA, USA). After vitrectomy the (undiluted) samples were frozen and stored at −80° C. until further use. After thawing the human vitreous samples, they were directly mixed with an equal volume of a dispersion of AuNPs (typically $10^{12}$ nanoparticles/ml in water). The samples were then allowed to equilibrate for 30 min at room temperature prior to applying (nanosecond) laser pulses.

The invention claimed is:

1. A method for the treatment of myodesopsia, wherein said treatment is a laser ablation treatment, and wherein said treatment comprises a composition arranged to be injected into the vitreous of an eye of a human or animal subject, the composition comprising particles for the treatment of myodesopsia as a light sensitizing agent, by attachment of the particles to collagen aggregates and treatment by irradiation inducing formation and collapse of nanobubbles, for removal of said aggregates, wherein each particle comprises a surface selected for providing mobility of said particle in the vitreous and for binding to collagen aggregates, wherein each of said particles comprises a core and wherein said surface is provided by a negatively charged coating on an exterior surface of said core, and wherein the laser ablation treatment further comprises binding of the particles of the composition to collagen aggregates in the vitreous and treatment by irradiating the particles in the vitreous bound to the collagen aggregates, thus locally exerting a mechanical force on the collagen aggregates when the particles are irradiated by laser light.

2. The method according to claim 1, wherein said particles form vapor nanobubbles in the vitreous when being irradiated.

3. The method according to claim 2, wherein said particles cluster around a vitreous opacity to concentrate an energy deposition by said laser ablation treatment near and/or in the vitreous opacity, such that expansion and/or shrinking of said vapor nanobubbles releases said mechanical force to dislodge and/or break apart said vitreous opacity.

4. The method according to claim 1, wherein said laser ablation treatment comprises irradiating at least part of the vitreous by laser pulses.

5. The method according to claim 4, wherein said laser pulses consist of one to 100 laser pulses per vitreous opacity.

6. The method according to claim 4, wherein said laser pulses have a length in the range of 10 fs to 10 ns.

7. The method according to claim 6, wherein said laser pulses have each a power density of $10^7$ to $10^{15}$ W/cm$^2$.

8. A method of ablation of vitreous opacities comprising the steps of:

injecting into the vitreous, a composition comprising particles for the treatment of myodesopsia as a light sensitizing agent, by attachment of the particles to collagen aggregates and treatment by irradiation of the particles in the vitreous bound to the collagen aggregates, thus inducing formation and collapse of nanobubbles, for removal of said aggregates, specifically binding the particles to collagen fibrils in the vitreous, and locally exerting a mechanical force in the vitreous by irradiating the particles with laser light, wherein each particle comprises a surface selected for providing mobility of said particle in the vitreous and for binding to the collagen aggregates, wherein each of said particles comprises a core and wherein said surface is provided by a negatively charged coating on an exterior surface of said core.

9. The method according to claim 1, wherein said coating comprises hyaluronic acid and/or a derivative thereof.

10. The method according to claim 1, wherein the particles comprise plasmonic metal.

11. The method according to claim 1, wherein said particles have a diameter in the range of 1 nm to 500 nm.

12. The method according to claim 1, wherein said particles have a diameter in the range of 1 nm to 10 nm.

* * * * *